United States Patent
Huang et al.

(10) Patent No.: US 11,432,719 B2
(45) Date of Patent: Sep. 6, 2022

(54) VISUAL FIELD SIMULATION USING OPTICAL COHERENCE TOMOGRAPHY AND OPTICAL COHERENCE TOMOGRAPHIC ANGIOGRAPHY

(71) Applicant: Oregon Health & Science University, Portland, OR (US)

(72) Inventors: David Huang, Portland, OR (US); Ou Tan, Portland, OR (US); Liang Liu, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 141 days.

(21) Appl. No.: 16/819,762

(22) Filed: Mar. 16, 2020

(65) Prior Publication Data
US 2020/0288971 A1 Sep. 17, 2020

Related U.S. Application Data

(60) Provisional application No. 62/818,648, filed on Mar. 14, 2019.

(51) Int. Cl.
*A61B 3/10* (2006.01)
*G06T 7/00* (2017.01)
(Continued)

(52) U.S. Cl.
CPC ............ *A61B 3/102* (2013.01); *A61B 3/1241* (2013.01); *G06T 7/0012* (2013.01); *G06T 7/11* (2017.01);
(Continued)

(58) Field of Classification Search
CPC ..... A61B 3/102; A61B 3/1241; G06T 7/0012; G06T 7/11; G06T 7/168; G06T 2207/10101; G06T 2207/20048; G06T 2207/20216; G06T 2207/30041; G06T 2211/404
See application file for complete search history.

(56) References Cited

U.S. PATENT DOCUMENTS

6,293,674 B1 * 9/2001 Huang ................... A61B 3/102
351/221
8,579,438 B2 * 11/2013 Hong ..................... A61B 3/102
351/206
(Continued)

FOREIGN PATENT DOCUMENTS

KR      101855012 B1 *  5/2018
WO   WO-2013126465 A1 *  8/2013  ........... A61B 3/1005
WO   WO-2019178100 A1 *  9/2019  ............... A61B 3/10

OTHER PUBLICATIONS

English translation of KR101855012B1 (Year: 2018).*

*Primary Examiner* — Jon Chang
(74) *Attorney, Agent, or Firm* — Schwabe Williamson & Wyatt, P.C.

(57) ABSTRACT

Disclosed herein are methods for simulating the results of a visual field (VF) test using an optical coherence tomography (OCT) system. The disclosed methods may utilize structural information extracted from OCT image datasets, such as thickness measurements, or may utilize functional information, such as blood perfusion measurements, extracted from OCT angiography (OCTA) image datasets. Other embodiments may be described and claimed.

28 Claims, 16 Drawing Sheets

(13 of 16 Drawing Sheet(s) Filed in Color)

(51) Int. Cl.
*G06T 7/11* (2017.01)
*A61B 3/12* (2006.01)
*G06T 7/168* (2017.01)

(52) U.S. Cl.
CPC .... *G06T 7/168* (2017.01); *G06T 2207/10101* (2013.01); *G06T 2207/20048* (2013.01); *G06T 2207/20216* (2013.01); *G06T 2207/30041* (2013.01); *G06T 2211/404* (2013.01)

(56) References Cited

U.S. PATENT DOCUMENTS

| | | | |
|---|---|---|---|
| 9,155,464 B2 * | 10/2015 | Tanaka | A61B 3/024 |
| 9,451,878 B2 * | 9/2016 | Yonezawa | G06T 7/0012 |
| 2008/0309881 A1 * | 12/2008 | Huang | A61B 3/024 |
| | | | 351/246 |
| 2015/0124216 A1 * | 5/2015 | Abramoff | A61B 3/0025 |
| | | | 351/206 |
| 2017/0055829 A1 * | 3/2017 | Tan | G06T 7/136 |

* cited by examiner

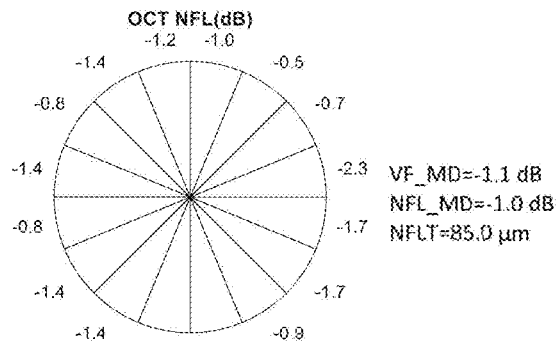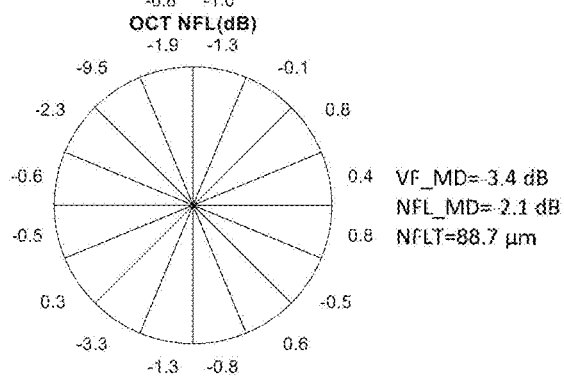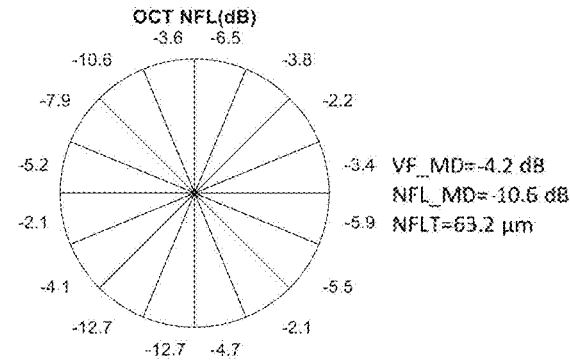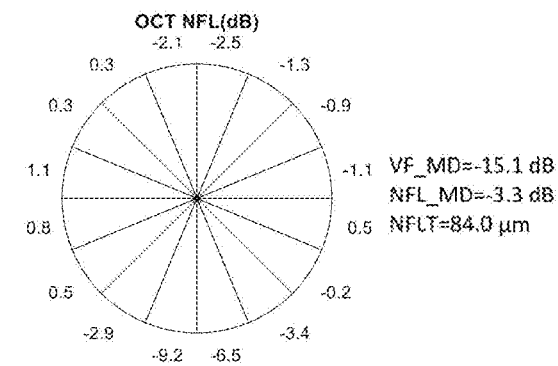
Figures 4A, 4B, 4C, and 4D

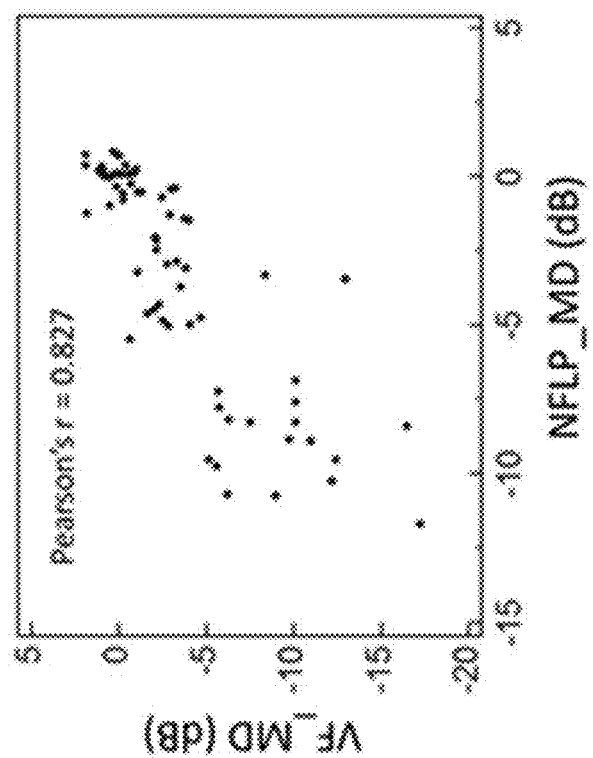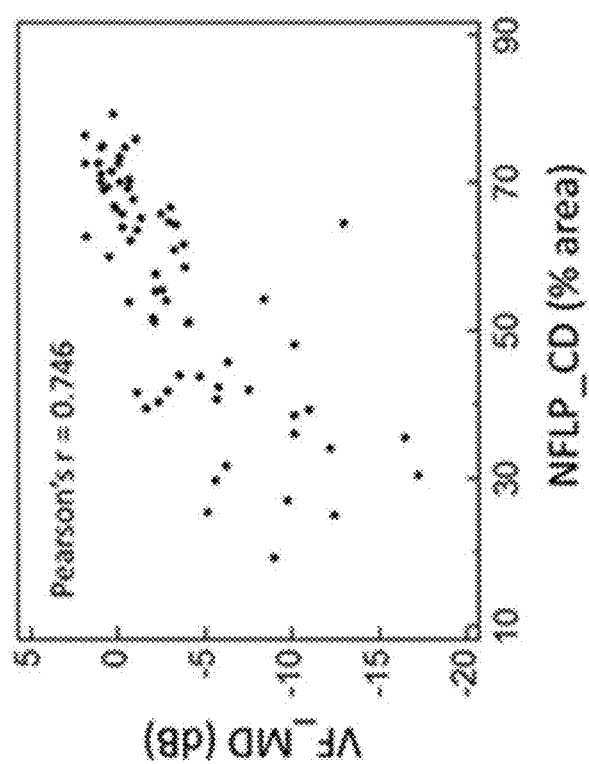
Figure 10

VISUAL FIELD SIMULATION USING OPTICAL COHERENCE TOMOGRAPHY AND OPTICAL COHERENCE TOMOGRAPHIC ANGIOGRAPHY

CROSS REFERENCE TO RELATED APPLICATION

This application claims priority to U.S. Provisional Application No. 62/818,648, which was filed on Mar. 14, 2019, and titled "VISUAL FIELD SIMULATION USING OPTICAL COHERENCE TOMOGRAPHY AND OPTICAL COHERENCE TOMOGRAPHIC ANGIOGRAPHY," the entire disclosure of which is hereby incorporated by reference.

STATEMENT OF GOVERNMENT SUPPORT

This invention was made with government support under R01 EY023285, R21 EY027007, and R01 EY013516 awarded by the National Institutes of Health. The government has certain rights in the invention.

FIELD

Generally, the field involves methods of imaging using optical coherence tomography. In particular, the field involves visual field simulation using optical coherence tomography (OCT) and OCT angiography.

BACKGROUND

Glaucoma is a leading cause of blindness, and effective glaucoma management requires early detection, followed by careful evaluation and monitoring to identify those at the highest risk for disease progression and vision loss. This allows the rational use of medical, laser, and surgical treatments, all of which have significant cost, compliance, and safety issues. The visual field (VF) test is the current standard to monitor glaucoma progression. However, VF testing is subjective, time-consuming, and poorly reproducible. Quantitative imaging of the optic nerve head (ONH) and retina with optical coherence tomography (OCT) are widely used in diagnosis and monitoring of glaucoma. But the overall peripapillary nerve fiber layer (NFL) thickness correlates poorly with VF mean deviation (MD). Furthermore, the speed of glaucoma progression as measured by OCT, such as NFL and macular ganglion cell complex (GCC) thinning in m/year, poorly correlates with the rate of VF changes as measured in MD trend in dB/year or Visual Field Index (VFI) trend in %/year. Thus it is difficult to clinically judge whether glaucoma is progressing rapidly or not based on OCT structural measurements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A, 4B, 4C, and 4D illustrate examples showing how nerve fiber layer-mean deviation (NFL_MD) could behave differently from visual field mean deviation (VF_MD) and overall nerve fiber layer thickness (NFLT) as diagnostic parameters, in accordance with various embodiments. Visual field (VF) total deviation maps are shown in the left column. The sectoral retinal nerve fiber layer (NFL) thickness in decibel (dB) scale is shown in the right column. FIG. 4A is for a normal eye with diffusely thin NFL; FIG. 4B is for an early perimetric glaucoma (PG) eye with focal VF and NFL defects; FIG. 4C is for an early PG eye with NFL_MD was more than 6 dB worse than VF_MD; FIG. 4D is for an advanced PG eye with NFL_MD more than 11 dB better than VF_MD.

FIG. 5A illustrates an analysis page for the ONH scan in the RTVue Software Version 6.12. Overall, hemisphere, quadrant and sectoral average NFL thickness are included in the output parameters. FIG. 5B illustrates the NFL thickness averaged in 16 sectors with arc lengths of 22.5°.

FIG. 6A illustrates the modified Garway-Heath visual field (VF) sectors. FIG. 6B illustrates the circumpapillary NFL thickness profile divided into 8 sectors that correspond to the 8 VF sectors. The weights in these sectors correspond to the number of VF test points. FIG. 6C illustrates the weights (numbers shown in the pie slices) for 16 evenly divided NFL sectors obtained by interpolation of the 8 sectors in FIG. 6B. MPA stands for maculopapillary axis.

FIG. 10 illustrates Pearson correlation of optical coherence tomographic angiography parameters and VF-MD, in accordance with various embodiments. NFLP_MD correlated with VF_MD better than NFLP_CD (P=0.001).

DETAILED DESCRIPTION

Figure 1:
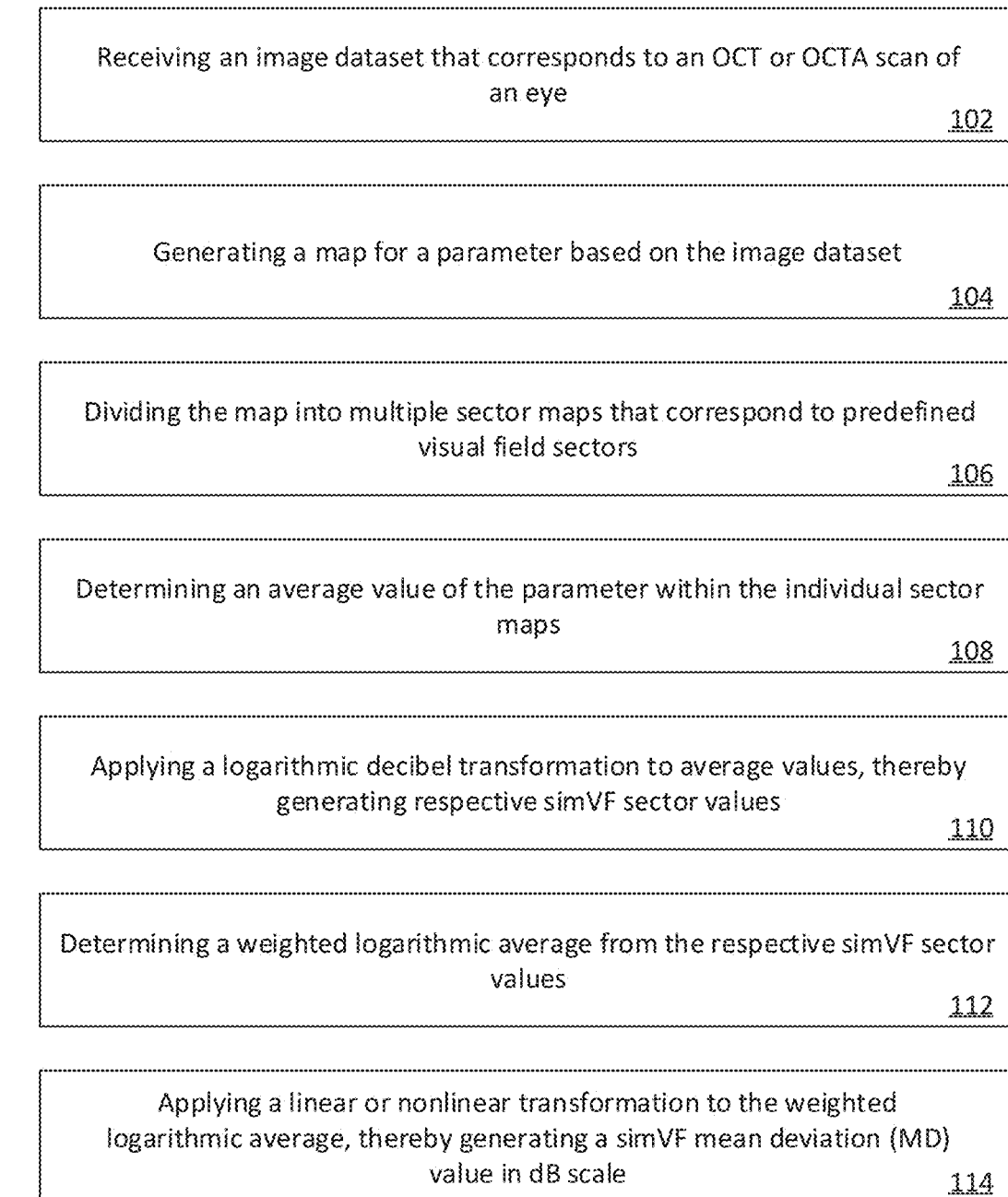
FIG. 1 is a flow chart of a method in accordance with various embodiments.

Disclosed herein are methods for simulating the results of a visual field (VF) test using an optical coherence tomography (OCT) system. The disclosed methods may utilize structural information extracted from OCT image datasets, such as thickness measurements, or may utilize functional information, such as blood perfusion measurements, extracted from OCT angiography (OCTA) image datasets.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

OCT provides structural measurements such as peripapillary retinal nerve fiber layer (NFL) and macular ganglion cell complex (GCC) thickness that are used to diagnose and monitor glaucoma and other optic nerve diseases. OCTA provides perfusion measurements such as the peripapillary nerve fiber layer plexus (NFLP) capillary density and macular superficial vascular complex (SVC) vessel density (VD) that are also used in glaucoma evaluation. Visual field (VF) is a subjective psychophysical test that is the gold standard to measure how glaucoma or other optic nerve and retinal diseases affects visual function. OCT and OCTA measurements are objective and more reproducible than VF measurements, but must be validated by VF. An impediment to glaucoma evaluation is that OCT and OCTA parameters do not correlate well with VF parameters. One obstacle is that VF is typically measured on a logarithmic decibel (dB) scale, which is more suitable for monitoring the progression of glaucoma. In contrast, structural OCT measurements are in linear micron thickness scale, and OCTA measurements are in linear vessel density (% area) scale. A second obstacle is that OCTA and OCT parameters are averaged with different spatial weights than the VF area or cortical area weighting used for VF parameters.

To address these limitations of OCT and OCTA, various embodiments herein provide a method to simulate VF using a conventional OCT or OCTA system. First, structural or perfusion maps are calculated from OCT or OCTA scans. The relevant OCT structural maps for glaucoma evaluation include the peripapillary nerve fiber layer (NFL) thickness map, circumpapillary NFL thickness profile, and/or the macular ganglion cell complex (GCC) thickness map. The relevant OCTA perfusion maps include the nerve fiber layer plexus (NFLP) capillary density (CD) map and/or the macular superficial vascular complex (SVC) vessel density (VD) map. Any of these maps may be used, or a combination of them may be be used to simulate VF.

In various embodiments, these fine-grained maps are divided into sectors that correspond to predefined VF sectors. The average value for the sector represents the sector map. The sector map is transformed to a logarithmic decibel (dB) scale that match the VF scale. This represents the simulated VF (simVF) sector map. The simVF sector values are then combined using VF area weighted averaging to obtain a weighted logarithmic average. The weighted logarithmic average is transformed (linearly or nonlinearly) to a simVF mean deviation (MD) value in dB scale that matches conventional VF_MD values. Instead of weights that corresponds to VF area, an alternative scheme uses weights that corresponds to area in the cerebral visual cortex. The weighted logarithmic average obtained in this fashion can be transformed to a global index call simVFI that corresponds to the conventional visual field index (VFI).

OCTA and OCTA-based sector and global simVF parameters show good agreement with actual VF parameters in terms of both the location and severity of glaucoma damage, especially in mild and moderate glaucoma. OCT and OCTA-based simVF parameters have better reproducibility than equivalent VF parameters. The simVF parameters have high diagnostic accuracy similar to conventional OCT and OCTA parameters. The simVF parameters have better correlation with actual VF parameters compared to the correlation between the original OCT thickness parameters and OCTA CD and VD parameters.

FIG. 1 illustrates an example process 100 for simulating a VF test using an OCT or OCTA system. The process 100 may include, at 102, receiving an image dataset that corresponds to an optical coherence tomography (OCT) or OCT angiography (OCTA) scan of an eye. For example, the OCT scan and/or OCTA scan may be of an optic nerve head and surrounding retina of the eye.

At 104, the process 100 may further include generating a map for a parameter based on the image dataset. For example, the map may be a thickness map for an OCT dataset or a perfusion map for an OCTA dataset. In some embodiments, the structural thickness map includes a peripapillary nerve fiber layer (NFL) thickness map, a circumpapillary NFL thickness map, or a macular ganglion cell complex (GCC) thickness map, or a combination thereof. The perfusion map may include, for example, a retinal nerve fiber layer plexus (NFLP) capillary density map or a macular superficial vascular complex (SVC) vessel density (VD) map. In some embodiments, the perfusion map may be generated by: segmenting a retinal layer within the image dataset; generating an en face angiogram from the segmented retinal layer; and generating the OCTA perfusion map from the en face angiogram.

At 106, the process 100 may include dividing the map into multiple sector maps that correspond to predefined visual field sectors. At 108, the process 100 may include determining an average value of the parameter within the individual sector maps. In some embodiments, the process 100 may further include (not shown in FIG. 1) extracting a thickness profile from the structural thickness map at a distance or range of distances from a center of the optic nerve head, wherein the average value corresponds to an average thickness value for a portion of the thickness profile that is within each sector map.

At 110, the process 100 may include applying a logarithmic decibel transformation to average values, thereby generating respective simVF sector values. In some embodiments, the average values may be scaled (e.g., to account for floor effects) prior to applying the logarithmic decibel transformation.

At 112, the process 100 may include determining a weighted logarithmic average from the respective simVF sector values. For example, values of the respective simVR sector maps may be weighted by visual field area or area in the cerebral visual cortex.

At 114, the process 100 may include applying a linear or nonlinear transformation to the weighted logarithmic average, thereby generating a simVF mean deviation (MD) value in dB scale. In some embodiments, applying the linear or nonlinear transformation may include applying a regression formula derived from population data.

Another example process for simulating a VF test using an OCT or OCTA system includes:

(1) receiving an OCT or OCTA scan of the retina, said scan comprising an image dataset;

(2) calculating an OCT map, OCT profile, or OCTA map for a parameter of interest using the image dataset;

(3) calculating an OCT sector map or OCTA sector map, wherein the sectors of the map correspond to predefined visual field sectors, and each sector is assigned a value based on the average value of the parameter of interest within said sector, (4) applying a logarithmic decibel transformation to the OCT or OCTA sector map, thereby generating a simVF sector map;

(5) calculating a weighted logarithmic average from the simVF sector map, wherein the sector map values are weighted by VF area for the averaging operation; and (6) applying a linear or nonlinear transformation to the weighted logarithmic average, thereby generating a simVF mean deviation (MD) value in dB scale.

In some embodiments, a process for simulating a VF test using an OCT system may include:

(1) receiving an OCT scan of the optic nerve head (ONH) and surrounding retina, said scan comprising an OCT image dataset;

(2) calculating a structural thickness map from the OCT image dataset, wherein the structural thickness map may comprise a peripapillary nerve fiber layer (NFL) thickness map, a circumpapillary NFL thickness map, or a macular ganglion cell complex (GCC) thickness map, or a combination thereof;

(3) dividing the structural thickness map into a plurality of sectors that correspond to predefined VF sectors;

(4) extracting a structural thickness profile from the structural thickness map at a prescribed distance (or over a range of distances) from the center of the ONH, for example along a circular path having a diameter between 1.0 mm and 5.0 mm (e.g., 3.4 mm) centered on the ONH;

(5) calculating for each sector an average sector thickness value;

(6) transforming the average sector thickness values to a logarithmic decibel (dB) scale, thereby generating a set of simVF sector thickness values (a simVF sector thickness map) having a dB scale. In some embodiments, sector thickness values are scaled before logarithmic transformation to account for floor value effects;

(7) combining the set of simVF sector thickness values using VF area weighted averaging, to generate a simVF weighted logarithmic average; and (8) transforming the simVF weighted logarithmic average to a simVF mean deviation (MD) value in dB scale that matches conventional VF_MD values.

In some embodiments, the weights of step (7) above may correspond to cortical area in the cerebral visual cortex rather than VF area, such that a cortical area weighted logarithmic average is calculated. In these embodiments, the cortical area weighted logarithmic average may further be transformed to a global index called simVFI that corresponds to conventional visual field index (VFI).

In some embodiments, a process for simulating a VF test using an OCT system may include:

(1) receiving an OCT scan of the optic nerve head (ONH) and surrounding retina, said scan comprising an OCT image dataset;

(2) calculating a thickness map from the OCT image dataset, wherein the thickness map may comprise a peripapillary nerve fiber layer (NFL) thickness map, a circumpapillary NFL thickness map, or a macular ganglion cell complex (GCC) thickness map, or a combination thereof;

(3) dividing the thickness map into a plurality of sectors that correspond to predefined VF sectors;

(4) extracting a thickness profile from the thickness map at a prescribed distance from the center of the ONH (for example, along a circular path having diameter of 3.4 mm and centered on the ONH);

(5) calculating for each sector an average thickness value for the portion of the thickness profile within said sector;

(6) scaling the average thickness values in each sector to account for floor value effects;

(7) transforming the scaled average thickness values in each sector to a logarithmic decibel (dB) scale, thereby generating a simulated VF sector map;

(8) calculating a weighted logarithmic average of the simulated VF sector map, wherein the weights are based on the VF area corresponding to NFL bundles passing through each peripapillary sector; and (9) transforming the weighted logarithmic average of the simulated VF sector map to a VF mean deviation (MD) value using a regression formula derived from population data.

In some embodiments, a circular scan pattern or a non-circular closed curve scan pattern may be used to acquire the OCT image dataset from which a thickness profile may be extracted.

In further embodiments, a process for simulating a VF test using an OCTA system may include:

(1) receiving an OCTA scan of the optic nerve head (ONH) and surrounding peripapillary retina, said scan comprising an OCTA image dataset;

(2) segmenting a retinal layer within the OCTA image dataset, for example the retinal nerve fiber layer plexus (NFLP) or the macular superficial vascular complex (SVC);

(3) generating an en face angiogram from the from the segmented retinal layer, for example using maximum flow projection;

(4) calculating an OCTA perfusion map from the en face angiogram and the OCTA image dataset, wherein the OCTA perfusion map may comprise a NFLP capillary density map or a macular superficial vascular complex (SVC) vessel density (VD) map.

(5) dividing the OCTA perfusion map into a plurality of sectors that correspond to predefined VF sectors (for example 16 sectors, 8 sectors, 4 sectors, or 2 sectors);

(6) calculating for each sector an average perfusion value;

(7) scaling the average perfusion values in each sector to account for floor value effects;

(8) transforming the scaled average perfusion values in each sector to a logarithmic decibel (dB) scale, thereby generating a set of perfusion-simulated VF values;

(9) converting the set of perfusion-simulated VF values to simulated sector visual field deviation values using a regression formula derived from population data;

(10) calculating a weighted logarithmic average of the simulated sector visual field deviation values, wherein the weights for each sector are proportional to the number of VF test point in the corresponding VF sector; and

(11) converting the weighted logarithmic average of the simulated sector visual field deviation to a VF mean deviation (MD) value using regression formula derived from population data.

Two example studies conducted by the present inventors are described below to demonstrate further details and example implementations of various embodiments.

Example 1—Estimating Visual Field Mean Deviation Using Optical Coherence Tomographic Nerve Fiber Layer Measurement in Glaucoma Patients Purpose:

To construct an optical coherence tomography (OCT) nerve fiber layer (NFL) parameter that has maximal correlation and agreement with visual field (VF) mean deviation (MD).

Methods:

The NFL_MD parameter in dB scale was calculated from the peripapillary NFL thickness profile nonlinear transformation and VF area-weighted averaging.

Results:

From the Advanced Imaging for Glaucoma study, 245 normal, 420 pre-perimetric glaucoma (PPG), and 289 perimetric glaucoma (PG) eyes were selected.

NFL_MD had significantly higher correlation (Pearson R: 0.66 vs 0.49) with VF_MD than the overall NFL thickness. NFL_MD also had significantly higher sensitivity in detecting PPG (0.13 vs 0.08) and PG (0.59 vs 0.43) at the 99% specificity level. NFL_MD had better reproducibility than VF_MD (0.35 vs 0.69 dB, p<0.001). The differences between NFL_MD and VF_MD were −0.31±1.87 dB, −0.02±2.46 dB and 3.47±3.74 dB and 7.30±3.92 dB for PPG, early PG, moderate PG, and severe PG subgroups, respectively.

Conclusion:

OCT-based NFL_MD has better correlation with VF_MD and greater diagnostic sensitivity than the average NFL thickness. It has better reproducibility than VF_MD, which may be advantageous in detecting progression. It agrees well with VF_MD in early glaucoma but underestimates damage in moderate~advanced stages.

INTRODUCTION

Glaucoma is a leading cause of blindness, and effective glaucoma management requires early detection, followed by careful evaluation and monitoring to identify those at the highest risk for disease progression and vision loss. This allows the rational use of medical, laser, and surgical treatments, all of which have significant cost, compliance, and safety issues. Visual field (VF) test is the current standard to monitor glaucoma progression. However, VF testing is subjective, time-consuming, and poorly reproducible. Quantitative imaging of the optic nerve head (ONH) and retina with optical coherence tomography (OCT)[3] are widely used in diagnosis and monitoring of glaucoma. But the overall peripapillary nerve fiber layer (NFL) thickness correlates poorly with VF mean deviation (MD). Furthermore, the speed of glaucoma progression as measured by OCT, such as NFL and macular ganglion cell complex (GCC) thinning in m/year poorly correlates with the rate of VF changes as measured in MD trend in dB/year or Visual Field Index (VFI) trend in %/year. Thus it is difficult to clinically judge whether glaucoma is progressing rapidly or not based on OCT structural measurements.

A major reason for the frequent discordance between OCT and VF results is the way in which they are scaled. OCT measures NFL and GCC in μm units, which is on a linear scale. VF maps and parameters are measured in decibel (dB) units on a logarithmic scale. Differences also exist in the strategy to provide summary data for OCT and VF testing. For example, the NFL thickness is weighted by the length along a peripapillary circle. In contrast, VF_MD is weighted by the VF area.

In this study, we hypothesized that reducing the differences in scaling and weighting could improve the correlation between VF and OCT measurements. We developed a method to estimate the VF_MD using the circumpapillary NFL thickness profile measured by OCT in the same eye. The method converts NFL thickness to a dB scale and averages it using VF area weighting. We then assessed whether the resulting NFL_MD has advantages over the commonly used overall NFL thickness in terms of diagnostic accuracy, staging accuracy, and correlation with VF_MD. Finally, the potential for more sensitive progression detection is evaluated by looking at between-visit retest variability.

Results

Characteristics of the Study Participants

Two hundred and forty-five normal eyes from 124 participants, 420 PPG eyes from 245 participants, and 289 PG eyes from 192 participants in the AIGS dataset had acceptable-quality OCT and VF data. Eyes in both the PPG and PG groups had significantly older age, longer axial length, worse VF PSD and MD, and thinner overall NFL thickness than the normal group (Table 1). In addition, eyes in PG group also had thinner central cornea than the normal. Although the age differences were statistically significant, they were small (2-3 years). In the PG group, 213 eyes had early PG (MD>−6 dB, stage 1), 47 eyes had moderate PG (MD between −6 and −12 dB, stage 2), 29 eyes had severe PG (MD<−12 dB, stage 3) according to the modified Hodapp-Parrish-Anderson (HPA) staging criteria. The PPG eyes had HPA stage 0, as their PSD and GHT values were normal by definition.

TABLE 1

Characteristics of the Study Population

| Characteristics | Normal (N) | Pre-perimetric Glaucoma (PPG) | p-value N v. PPG | Perimetric Glaucoma (PG) | p-value N v. PG |
|---|---|---|---|---|---|
| Number of participants (eyes) | 124 (245) | 245 (420) | N/A | 192 (289) | N/A |
| Age (years) | 58.0 ± 9.3 | 61.3 ± 9.5 | 0.001 | 62.3 ± 9.6 | <0.001 |
| Female (%) | 64.5 | 60.8 | 0.388 | 59.4 | 0.536 |
| Axial length (mm) | 23.7 ± 1.0 | 24.3 ± 1.3 | <0.001 | 24.3 ± 1.3 | <0.001 |
| Corneal thickness (μm) | 562 ± 33 | 556 ± 37 | 0.180 | 544 ± 37 | <0.001 |
| IOP (mmHg) | 14.3 ± 2.2 | 14.5 ± 2.8 | 0.750 | 13.8 ± 3.3 | 0.036 |
| VF MD (dB) | −0.1 ± 1.1 | −0.3 ± 1.1 | <0.001 | −4.4 ± 4.4 | <0.001 |
| VF PSD (dB) | 1.5 ± 0.3 | 1.7 ± 0.5 | <0.001 | 5.6 ± 4.1 | <0.001 |
| Overall NFLT (μm) | 99.7 ± 8.4 | 90.9 ± 10.0 | <0.001 | 80.2 ± 11.3 | <0.001 |

The characteristics of the study participants were averaged over the 4 consecutive study visits except for axial length and central corneal thickness, which were only measured at baseline.
IOP = intraocular pressure;
VF = visual field;
MD = mean deviation;
PSD = pattern standard deviation;
NFLT = nerve fiber layer thickness.

Normal Reference and Floor Values

The normative reference values for sector and overall NFL thickness were calculated from 245 normal participants with age and axial length correction (Table 2).

The floor value as a percentage of the reference NFL thickness was found to be 45% by pooling all sectors. The simplifying assumption that the floor percentage is the same for all sectors was necessary as the worst sectors were always found to be inferotemporal or superotemporal. The floor percentage was similar among the inferotemporal and superotemporal sectors with no clear pattern of difference.

TABLE 2

Intercept and slope for overall and sectoral NFL thickness estimation

| | | Y-Intercept (μm) | Age (μm/year) | Axial Length (μm/mm) |
|---|---|---|---|---|
| Overall NFL Thickness | | 188.0 | −0.14 | −3.38 |
| Inferior quadrant NFL thickness | | 246.3 | −0.10 | −4.93 |
| Sectoral NFL Thickness | TU1 | 124.1 | −0.14 | −2.06 |
| | TU2 | 141.1 | −0.13 | −1.64 |
| | ST2 | 199.4 | −0.26 | −2.30 |
| | ST1 | 225.9 | −0.12 | −3.54 |
| | SN1 | 187.5 | −0.08 | −3.06 |
| | SN2 | 202.5 | −0.29 | −3.31 |
| | NU2 | 235.9 | −0.32 | −5.19 |
| | NU1 | 203.5 | −0.17 | −5.00 |
| | NL1 | 151.6 | −0.07 | −3.39 |
| | NL2 | 189.1 | −0.13 | −4.22 |
| | IN2 | 241.2 | −0.19 | −5.40 |
| | IN1 | 332.9 | −0.07 | −8.71 |
| | IT1 | 290.0 | −0.05 | −5.98 |
| | IT2 | 121.9 | −0.10 | 0.36 |
| | TL2 | 72.5 | −0.15 | 0.51 |
| | TL1 | 89.0 | −0.03 | −1.18 |

Agreement Between NFL and VF Parameters

Figure 2:
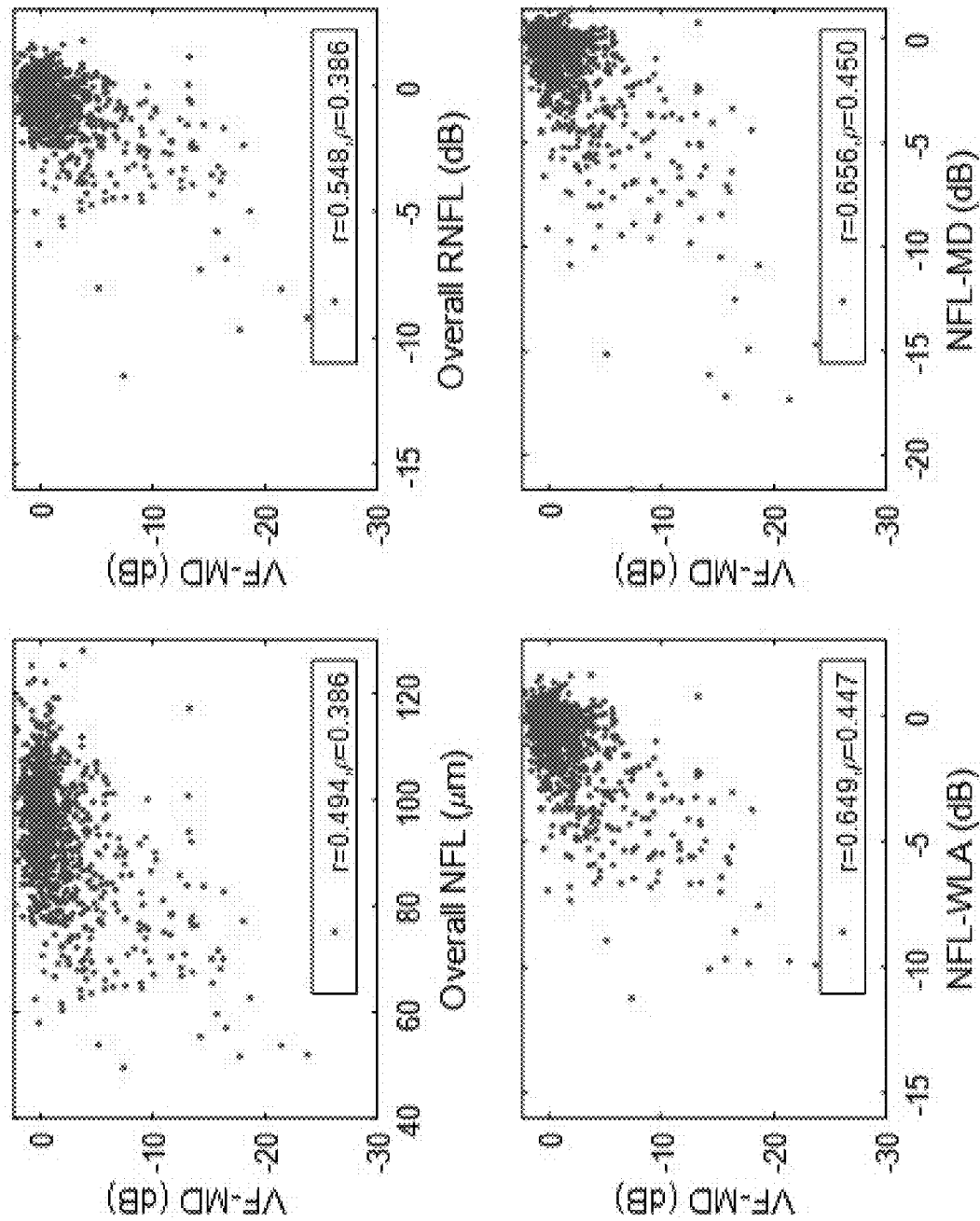
FIG. 2 illustrates the correlation of optical coherence tomography retinal nerve fiber layer (NFL) parameters and visual field mean deviation (VF_MD), in accordance with various embodiments. Abbreviations shown in FIG. 2: r is the Pearson correlation coefficient; p is the Spearman's rank correlation coefficient; and WLA is the weighted logarithmic average.

The overall average NFL thickness in μm had fair correlation with VF_MD, but the relationship was highly non-linear (FIG. 2). This was improved by simply converting from μm to dB scale (FIG. 2). Altering the NFL averaging procedure to use dB scale and VF area weighting yielded $NFL_{WLA}$, which had even better correlation with VF_MD (FIG. 2). Removing the residual nonlinearity yielded NFL_MD, which had the best correlation with VF_MD (FIG. 2). In the five-fold cross validation used to evaluate NFL_MD performance, the quadratic formulas is slightly different for each fold. The quadratic formula based on the fitting of all participants is:

$$NFL\_MD = 0.864 * (NFL_{WLA}) - 0.075 * (NFL_{WLA})^2$$

The correlation between NFL_MD and VF_MD was significantly ($p<0.001$) higher than that between overall NFL average (either in μm or dB scale) and VF_MD, for both Pearson and Spearman coefficients (FIG. 2).

TABLE 3

Mean Deviations, Cataract Density, and Visual Acuity Stratified by Glaucoma Severity

| Parameter | Normal | PPG | Early PG | Moderate PG | Severe PG |
|---|---|---|---|---|---|
| VF_MD (dB) | −0.03 ± 1.07 | −0.47 ± 1.39 | −2.48 ± 1.68 | −8.55 ± 1.66 | −15.19 ± 2.71 |
| NFL_MD (dB) | −0.17 ± 0.61 | −0.79 ± 1.26 | −2.46 ± 2.35 | −5.08 ± 3.52 | −7.89 ± 4.83 |
| NFL_MD − VF_MD (dB) | −0.14 ± 1.14 | −0.31 ± 1.87 | 0.02 ± 2.46 | 3.47 ± 3.74 | 7.30 ± 3.92 |
| Cataract (0-4) | 0.59 ± 0.52 | 0.77 ± 0.59 | 0.92 ± 0.59 | 0.80 ± 0.52 | 0.76 ± 0.56 |
| BCVA (LogMAR) | −0.03 ± 0.09 | 0.00 ± 0.08 | 0.02 ± 0.08 | 0.01 ± 0.08 | 0.06 ± 0.08 |

Group mean ± standard deviation. The best-corrected visual acuity (BCVA) was analyzed in the form of the logarithm of minimum angle of resolution (logMAR). LogMAR values of 0, 0.1, and 0.2 are equivalent to Snellen acuity of 20/20, 20/25, and 20/32.

Figure 3:
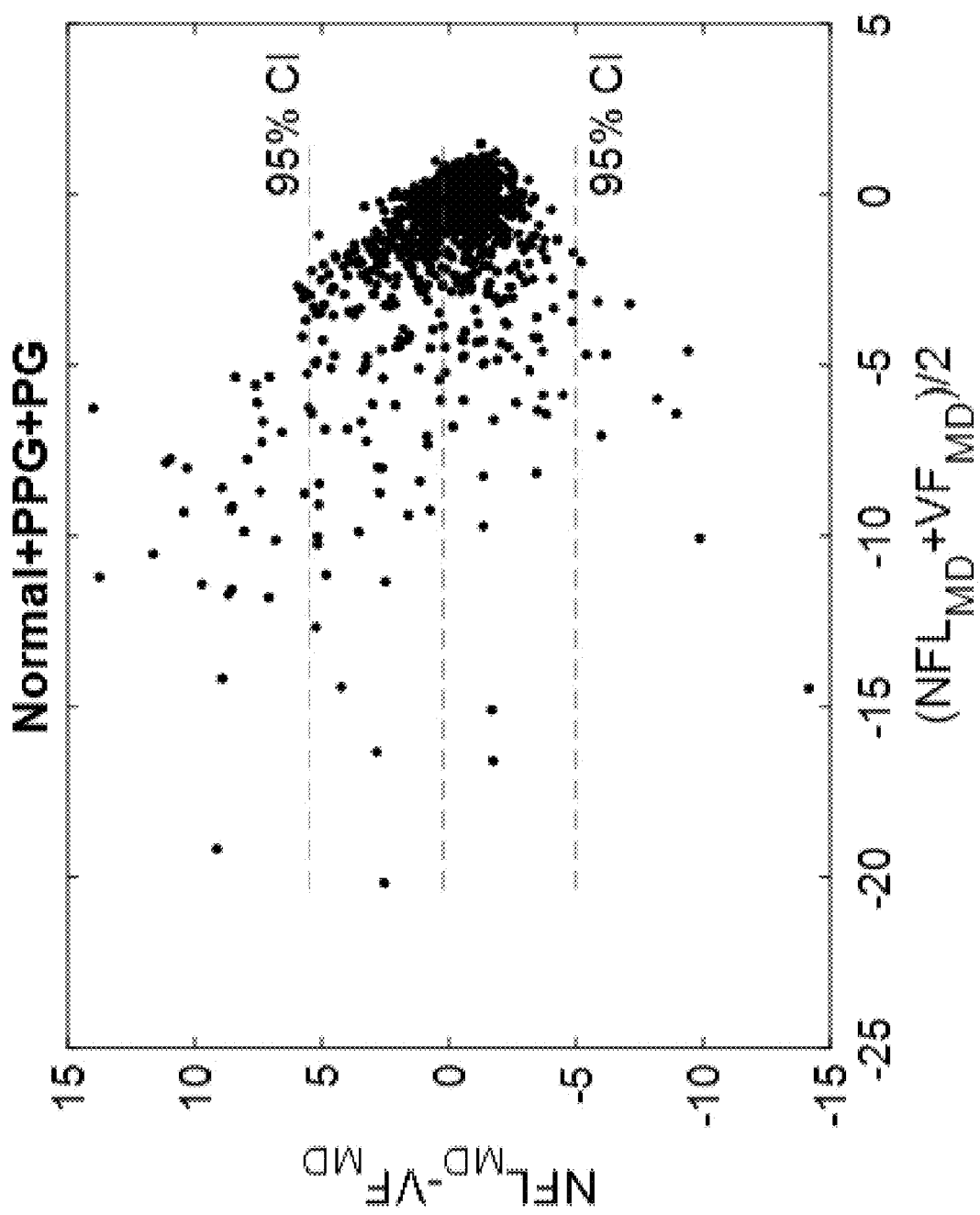
FIG. 3 illustrates a Bland-Altman analysis of the agreement between nerve fiber layer-mean deviation (NFL_MD) and visual field-mean deviation (VF_MD), in accordance with various embodiments. Data from normal, pre-perimetric glaucoma, and perimetric glaucoma groups are combined.

Difference analysis (Table 3) and Bland-Altman analysis (FIG. 3) showed that the agreement between NFL_MD and VF_MD was good in PPG group, fair in the early PG group, and poor in the moderate PG group and advance-to-severe PG group. There was an average bias toward better NFL_MD than VF_MD in the moderate to severe PG groups. The standard deviation of the difference between NFL_MD and VF_MD increased with increasing glaucoma severity. There were several outliers in the PPG, early PG, and moderate PG groups that had much worse NFL_MD than VF_MD (FIG. 3, FIG. 4). Whereas the NFL_MD was generally better than the VF_MD in the advanced-to-severe PG group. Overall, NFL_MD agreed well with VF_MD in PPG and early PG stages. But in the later stages of glaucoma (moderate to severe PG), NFL_MD tend to underestimate glaucoma severity, in comparison to VF_MD.

One possible explanation for the discrepancy between NFL_MD and VF_MD in the moderate-to-severe PG stages is cataract severity. Therefore, we examined cataract severity and BCVA in the different stages of glaucoma (Table 3). No significant difference between stages was found.

The agreement between NFL_MD and VF_MD staging of glaucoma severity was compared using the modified Hodapp-Parrish-Anderson classification (Table 4). The NFL_MD staging is based on the value of NFL_MD only: Stage 0-1, NFL_MD>=−6 dB; stage 3, NFL_MD<−6 dB. The F1 score was used to assess agreement. The F1 score was a better metric than kappa as a metric for agreement in this case because of the imbalance in the chi-square tables (Table 4). The classification agreement was excellent in the PPG group (F1 score 0.99) and good in the PG group (F1 score 0.87). In the PG group, there was a tendency for NFL_MD to under-estimate glaucoma severity stage, compared to VF_MD.

TABLE 4

Staging Agreement between Nerve Fiber Layer and Visual Field Mean Deviations

| | | NFL_MD | | | |
|---|---|---|---|---|---|
| | | PPG eyes | | PG eyes | |
| | | Stage 0-1 | Stage 2-3 | Stage 0-1 | Stage 2-3 |
| VF_MD | Stage 0-1 | 417 | 3 | 201 | 14 |
| | Stage 2-3 | 0 | 0 | 45 | 29 |

The modified Hodapp-Parrish-Anderson glaucoma staging system was used.
Abbreviations: NFL—nerve fiber layer; MD—mean deviation; PPG—pre-perimetric glaucoma; PG—perimetric glaucoma; VF—visual field.

TABLE 5

Reproducibility of Mean Deviation for Visual Field & Optical Coherence Tomography

| Parameter | PPG | Early PG | Moderate PG | Severe PG |
|---|---|---|---|---|
| VF_MD (dB) | 0.62 | 0.70 | 0.84 | 1.18 |
| NFL_MD (dB) | 0.23 | 0.42 | 0.68 | 0.45 |
| p-value | <0.001 | <0.001 | 0.22 | 0.003 |

The reproducibility of visual field mean deviation (VF_MD) and OCT-based retina nerve fiber layer-mean deviation (NFL_MD) were estimated by the root-mean-square residual of linear regression from 4 consecutive visits.

In aggregate analysis of all groups, NFL_MD had similarly excellent ICC as overall NFL thickness for both within-visit repeatability (0.988 vs 0.988) and between-visit reproducibility (0.978 vs 0.968).

The reproducibilities of NFL_MD and VF_MD were also assessed by the pooled root-mean-square residual of linear regression over 4 consecutive visits in glaucoma eyes (Table 5). This could be viewed as the standard deviation between visits adjusted for the glaucoma progression trend between visits. Overall, NFL_MD has better reproducibility than VF_MD (0.35 vs 0.69 dB, p<0.001). For both NFL_MD and VF_MD, the reproducibility was best at the earliest stage of glaucoma and worsened in the more severe stages. NFL_MD had better reproducibility than VF_MD at all stages and the difference is significantly in PPG and early PG stages.

The diagnostic accuracy of NFL_MD was compared with VF_MD and the two best NFL diagnostic parameters on linear micron scales (Table 6). For the discrimination between PPG and normal groups, NFL_MD had significantly (p<0.001) better diagnostic accuracy, as measured by AROC, than overall NFL thickness. NFL_MD also had both higher diagnostic sensitivity at the 95% and 99% specificity cutoff (p<=0.001, McNemar test) than overall NFL thickness, and inferior NFL thickness (p<=0.01). For discrimination between the PG and normal groups, NFL_MD had significantly (p<0.013) higher AROC than both micron-scale NFL parameters, and significantly (p<0.006) higher sensitivity than both micron-scale NFL parameters at both 95% and 99% specificity. NFL_MD also had higher sensitivity than VF_MD at 99% specificity (p=0.001). Other differences between NFL_MD and other parameters were not statistically significant. Overall, the consistent pattern was that NFL_MD had better diagnostic accuracy than micron scale NFL parameters. The diagnostic thresholds for NFL_MD was tighter than those for VF_MD because of smaller variation within the normal group.

TABLE 6

Diagnostic Accuracy of Nerve Fiber Layer-Mean Deviation Compared to Other Optical Coherence Tomography and Visual Field Parameters

| Discrimination Task | Parameter | AROC Mean ± SD | Sensitivity 95% Specificity | Sensitivity 99% Specificity | Cutoff 95% Specificity | Cutoff 99% Specificity |
|---|---|---|---|---|---|---|
| Pre-Perimetric Glaucoma v. Normal | Overall NFLT | 0.626 ± 0.023* | 0.172* | 0.076* | 87.7 | 82.3 |
| | Inferior NFLT | 0.644 ± 0.023 | 0.205* | 0.089* | 105.3 | 97.3 |
| | NFL_MD | 0.656 ± 0.023 | 0.256 | 0.131 | −1.21 | −1.76 |
| Perimetric Glaucoma v. Normal | VF_MD | 0.915 ± 0.013 | 0.646 | 0.461* | −2.00 | −3.32 |
| | Overall NFLT | 0.844 ± 0.019* | 0.556* | 0.428* | 87.7 | 82.3 |
| | Inferior NFLT | 0.861 ± 0.018* | 0.643* | 0.534* | 105.3 | 97.3 |
| | NFL_MD | 0.889 ± 0.016 | 0.695 | 0.593 | −1.21 | −1.76 |

Area under receiver operating characteristic curve (AROC) for visual field mean deviation (VF_MD) and OCT-based retinal nerve fiber layer (NFL) parameters. The NFL parameters are overall average NFL thickness (overall NFLT), inferior quadrant NFLT (Inferior NFLT) and NFL mean deviation (NFL_MD).
*P-value < 0.05 comparing to BFL_MD
— diagnostic accuracy of VF-MD is not calculated because VF is in the selection criteria of pre perimetric glaucoma Several examples are shown to give insight on why NFL_MD might perform differently from overall NFL thickness (micrometer scale) and VF_MD (FIGS. 4A-4D). The example in FIG. 4A shows that overall NFL thickness could be abnormally low in a normal eye with uniformly thin NFL, but yet NFL_MD could remain within normal limits. This demonstrates how NFL_MD could have improved diagnostic specificity over NFL thickness in people with normally thin NFL. In FIG. 4B, NFL_MD was abnormal due to focal defects in the superotemporal and inferotemporal sectors while the overall NFL thickness remained within normal range because other sectors had above normal thickness (positive sector dB values). This demonstrates how NFL_MD could have improved diagnostic sensitivity because the logarithmic (dB) scale and VF area weighting emphasized focal thinning in the characteristic glaucoma pattern. FIG. 4C shows an early PG eye where NFL_MD was much worse than VF_MD, probably because the eye already started with thin NFL prior to glaucoma damage— the pattern of NFL thinning was both diffuse and focal. FIG. 4D shows an advanced PG eye where the NFL_MD was much better than VF_MD, probably because the eye started with thicker than average NFL—in sectors less affected by glaucoma the NFL thickness remained above average (positive dB values).

Discussion

Visual field and OCT measurements are both commonly used for the diagnosis and monitoring of glaucoma. Unfortunately, VF parameters and OCT-based NFL thickness parameters do not correlate well with each other. This poses challenges in the staging and monitoring of glaucoma, given the potential for discordant functional and structural results.

One reason for the low correlation between NFL and VF is the disparate scales on which they are measured. NFL thickness parameters (e.g., overall, quadrant, octant, and sector averages) are measured using a linear μm scale, while VF parameters (e.g., mean deviation, pattern standard deviation, and visual field index) are measured in dB using a logarithmic scale. To harmonize the two types of measurements, Malik et al. suggested that the correlation between VF and NFL should be either in linear to linear scale or logarithm-logarithm scale. See Malik, R., Swanson, W. H. & Garway-Heath, D. F. 'Structure-function relationship' in glaucoma: past thinking and current concepts. *Clin Exp Ophthalmol* 40, 369-380, doi:10.1111/j.1442-9071.2012.02770.x (2012).

To convert OCT measurements to a scale more consistent with VF testing, investigators have used quadratic, broken stick and logarithmic transformations. Machine learning has also been used to transform OCT information into estimates of retinal sensitivity (a VF measure). In Kihara's deep learning model, localized slices from B-scans was directly used to estimate the retinal sensitivity point-by-point using a convolutional neural network with a regression output. See Kihara, Y. et al. Estimating Retinal Sensitivity Using Optical Coherence Tomography With Deep-Learning Algorithms in Macular Telangiectasia Type 2. *JAMA Netw Open* 2, e188029, doi:10.1001/jamanetworkopen.2018.8029 (2019).

Other investigators have converted VF results to a linear scale. Hood et al. suggested a linear model to relate NFL thickness and VF sector retinal sensitivity (linear 1/Lambert unit) (Hood, D. C., Anderson, S. C., Wall, M. & Kardon, R. H. Structure versus function in glaucoma: an application of a linear model. *Invest Ophthalmol Vis Sci* 48, 3662-3668, doi:10.1167/iovs.06-1401 (2007)), using a modified Garway-Heath sector scheme (Garway-Heath, D. F., Poinoosawmy, D., Fitzke, F. W. & Hitchings, R. A. Mapping the visual field to the optic disc in normal tension glaucoma eyes. *Ophthalmology* 107, 1809-1815 (2000)). Hood also showed that it is necessary to subtract the NFL thickness floor value in order to find the best correspondence with linearized VF measures. Wu et al. used the similar model on a different structure-function correspondence map generate by Kanamori et al. See Wu, H., de Boer, J. F., Chen, L. & Chen, T. C. Correlation of localized glaucomatous visual field defects and spectral domain optical coherence tomography retinal nerve fiber layer thinning using a modified structure-function map for OCT. *Eye (Lond)* 29, 525-533, doi:10.1038/eye.2014.317 (2015).

We believe that converting OCT measurements to a logarithmic scale is a superior strategy for determining the rate of disease progression, as compared to converting VF parameters to a linear scale. Caprioli et al. showed that the worsening of VF_MD, on the usual dB scale, decelerates with respect to time in the more advanced stages. See Caprioli, J. et al. A method to measure and predict rates of regional visual field decay in glaucoma. *Invest Ophthalmol Vis Sci* 52, 4765-4773, doi:10.1167/iovs.10-6414 (2011). If VF_MD is transformed from dB to linear scale, this nonlinearity would be even more exaggerated, with rapid progression in the early stages and very little change in the later stages. Indeed this is what is found when glaucoma is monitored with OCT NFL measurements on a linear micron scale—there is more rapid progression in early stages and almost no change in the advanced stage. It makes sense that in advanced stages of glaucoma, when there few retinal nerve fibers remain, there would be very little further thinning of the NFL. Yet it is important to monitor the rate of thinning as a percentage of what remains, as even a few μm of thinning at the advanced stages could have large impact on vision and quality of life. Thus, using a logarithmic (dB) scale to measure glaucoma may facilitate change detection across the entire spectrum of glaucomatous disease severity.

In order to improve the correlation with VF_MD, it is insufficient to simply transform the overall NFL thickness from a μm to dB scale. It is necessary to perform the logarithmic transformation on a point or sector basis, and then perform the averaging operation using weights that are proportional to VF area. We demonstrated that this NFL weighted logarithmic average, compared to a simple logarithmic transform of the NFL average thickness, was better correlated with VF_MD. This result is consistent with the finding by some investigators that the correlation between VF and NFL is higher for sectors averages than overall average.

The NFL-weighted logarithmic average still exhibited a floor effect in eyes with moderate-to-severe glaucoma. Thus a final quadratic fit was used to obtain the NFL_MD, an OCT-based optimized estimate for VF_MD. Compared to overall NFL thickness using a linear scale, NFL_MD demonstrated much better correlation with VF_MD. The agreement between NFL_MD and VF_MD are good in the PPG and early PG stages, however, NFL_MD still significantly underestimated VF damage in the moderate PG stage and markedly under-estimated VF damage in the advanced-to-severe stages. Thus the clinician needs to exercise caution in applying NFL_MD to glaucoma staging.

There are several reasons for this discrepancy. The lower limit of −12.8 dB we placed on sector NFL value is not nearly as low as the worst VF total deviation on a pointwise basis, which has a bottom limit of −33 dB on the Humphrey Field Analyzer. While we could lower the bottom limit to extend the dynamic range of NFL_MD, this would significantly worsen the repeatability from NFL measurement noise. Since our primary goal for developing the NFL_MD was to improve glaucoma monitoring, we want to maintain the reproducibility of NFL_MD over VF_MD across all stages of glaucoma. Thus some remaining discrepancy in the advanced stages of glaucoma may be unavoidable. Other reasons for discrepancy between NFL_MD and VF_MD include cataract, other media opacities and optical aberrations, dry eye, and psychophysical limitations on the subject's test taking ability. These may explain some outlier points where VF_MD was poor while NFL_MD was near normal. In these cases, NFL_MD may provide a more accurate assessment of glaucoma severity than VF_MD. On the other hand, error in NFL_MD could be introduced by image processing (e.g., segmentation) error and anatomic changes such as retinal edema and epiretinal membrane.

The largest source of discrepancy may be unavoidable variation in NFL thickness within the normal population. The standard deviation of overall NFL thickness in our sample was 8.4 μm, 8.5% of the normal average value of 99.7 μm. Thus 95% confidence interval of NFL_MD would be −1.5 to +0.9 dB simply from normal population variation. If the eye were to have −6 dB (75%) loss of nerve fibers from baseline, the 95% confidence interval due to the variation from their starting point would be −14.1 to −5.0 dB according to our NFL_MD formula. Thus one can see that the agreement between NFL_MD and VF_MD would deteriorate in the more advanced stages of glaucoma simply due to the variation in normal NFL thickness and its floor value. Although we have reduced this variation by adjusting for age and axial length, most of this variation is random and cannot be adjusted for. Thus the use of NFL_MD in the staging of glaucoma would always be hampered by the fact that each of us is born with a different NFL thickness.

Compared to conventional um-scale NFL thickness, NFL_MD correlates better with VF_MD. But this correlation is still not good in moderate and severe glaucoma stages, and this poses a limitation for the monitoring of glaucoma progression. For the objective monitoring of glaucoma progression in the more advanced stages, structural OCT measurement of the macular ganglion cell complex and optical coherence tomographic angiography (OCTA) measurements of perfusion may perform better. The methods developed here to improve VF correlation and diagnostic accuracy could be applied to those other OCT and OCTA measurements as well.

We found that NFL_MD had significantly better glaucoma detection sensitivity at both 95% and 99% specificity diagnostic cut-points, compared to VF_MD and the best conventional NFL diagnostic parameters (overall average and inferior quadrant). While we did not intentionally optimize NFL_MD for glaucoma diagnosis, we believe the improved diagnostic performance is due to the weighted logarithmic averaging step. Converting the sector NFL measurements to a dB scale emphasizes focal defect. And weighting by VF area emphasizes the inferior and superior arcuate areas most often affected by glaucoma. To illustrate, a 5% uniform diffuse loss of NFL thickness in an average normal eye would yield an NFL_MD of −0.22 dB, well within the normal range. But a 55% loss in the inferior-most inferotemporal sector (16-division sectors), while still giving a 5% reduction in overall average NFL thickness (still within normal range), would yield an NFL_MD of −1.89 dB, which crosses the 99%-specificity diagnostic threshold for glaucoma. Glaucoma damage in the early stages tend to be focal and most likely in the sectors weighted most by VF area (inferotemporal and superotemporal). Thus the higher diagnostic accuracy NFL_MD may be due to its ability to accentuate focal loss in any of the likely sectors.

In conclusion, we have developed a method to simulate VF_MD based on OCT NFL measurements. The resulting parameter is called NFL_MD. Compared to conventional NFL parameters, NFL_MD has improved correlation with VF_MD. NFL_MD is on a dB scale that corresponds to VF_MD, and thus the speed of glaucoma progression measured by NFL_MD is easier to interpret than conventional NFL parameters. NFL_MD has better reproducibility than VF_MD, thus it may allow earlier detection of significant glaucoma progression. We plan to study the use of NFL_MD in monitoring glaucoma progression using the AIG dataset in upcoming publications.

Method

Data

Data from the Advanced Imaging for Glaucoma (AIG) study were analyzed in this study. AIG was a bioengineering partnership (R01 EY013516) and multi-site longitudinal prospective clinical study sponsored by the National Eye Institute (ClinicalTrials.gov identifier: NCT01314326). The study design and baseline participant characteristics are according to Le, P. V. et al. Advanced imaging for glaucoma study: design, baseline characteristics, and inter-site comparison. *Am J Ophthalmol* 159, 393-403 e392, doi:10.1016/j.ajo.2014.11.010 (2015), and the Manual of Procedures is publically available online (www.AIGStudy.net). The study procedures adhered to the Declaration of Helsinki, which guides studies involving human subjects. Written informed consent was obtained from all patients for the participation in the study. Proper institutional review board approvals were obtained from all participating institutions. The study was in accordance with the Health Insurance Portability and Accountability Act of 1996 (HIPAA) privacy and security regulations. This study was approved by the Institutional Review Board (IRB) of Oregon Health&Science University.

In this study, data collected from the normal (N), pre-perimetric glaucoma (PPG) and perimetric glaucoma (PG) participants from the AIG study were analyzed.

Both eyes of normal participants met the following criteria: VF tests within normal limits, IOP<21 mm Hg, and normal optic nerve on slit-lamp biomicroscopy.

Eyes enrolled in the PPG group had glaucomatous optic neuropathy as evidenced by diffuse or localized thinning of the neuroretinal rim or NFL defect on fundus examination, but normal VF with pattern standard deviation (PSD, P>0.05) and glaucoma hemifield test (GHT) within normal limits.

Eyes enrolled in the PG group had glaucomatous optic neuropathy as evidenced by diffuse or localized thinning of the neuroretinal rim or NFL defect on fundus examination, and corresponding repeatable VF defects with PSD (P<0.05) or GHT outside normal limits.

Exclusion criteria common to all groups included best-corrected visual acuity (BCVA) worse than 20/40, evidence of retinal pathology, or history of keratorefractive surgery. Cataract was not an exclusion criteria for AIG enrollment, but the cataract density (grade 0 to 4) was recorded. For the analysis in this article, we excluded eyes with cataract density worse than 2 or BCVA worse than 20/30 during any of the 4 visits analyzed in this article.

Normal participants were followed every 12 months and glaucoma participants were followed every 6 months. OCT and VF testing were performed at all follow-up and baseline visits for PG/PPG participants. In order to improve the repeatability of the measurements in the same eye, we averaged measurements from the 4 earliest consecutive visits that had complete OCT and VF data for glaucoma participants.

Visual Field Testing

The visual field was assessed by standard automated perimetry on the Humphrey Field Analyzer (HFA II; Carl Zeiss Meditec, Inc, Dublin, Calif., USA) using the Swedish Interactive Thresholding Algorithm 24-2. The minimum requirement for reliability included less than 15% fixation losses, less than 33% false positives, and less than 33% false negatives. The VF test was done at baseline for all participants, and then every 6 months for glaucoma participants and every 4 years for normal participants.

Nerve Fiber Layer Thickness Measurement and Conversion to Decibel Scale

Spectral-Domain Optical Coherence Tomography

Participants were scanned with spectral domain OCT (RTVue, Optovue, Inc, Fremont, Calif., USA), the optic nerve head (ONH) and 3-D Disc scans were used to map the optic nerve head and nerve fiber layer. Three ONH scans were obtained in each visit for disc and NFL thickness measurements. One Disc 3D scan was obtained at the baseline visit. The OCT data were export from the OCT machine of each clinical center and send to the OCT reading center for grading. In the OCT reading center, OCT data were analyzed using REVue software (Version 6.12, Optovue). Firstly, the center of the optic disc was identified on the Disc 3D scan was and used to register the disc positions in all subsequent ONH scans. Then NFL thickness maps (1.3~4.9 mm) were first measured from the ONH scans. Then a NFL thickness profile was resampled on a 3.4-mm diameter circle centered on the disc. The process is automated but the grader needs to validate the data to exclude scans with poor SSI, cropping or failed segmentation. Scans with failed segmentation, cropping, low signal strength index (SSI<37), or decentration>0.75 mm were excluded from further analysis. Among the repeated ONH scans in the same visit, one scan is randomly picked for further analysis and comparison to the single VF test available for each visit.

Sector NFL thickness

Figure 5B:
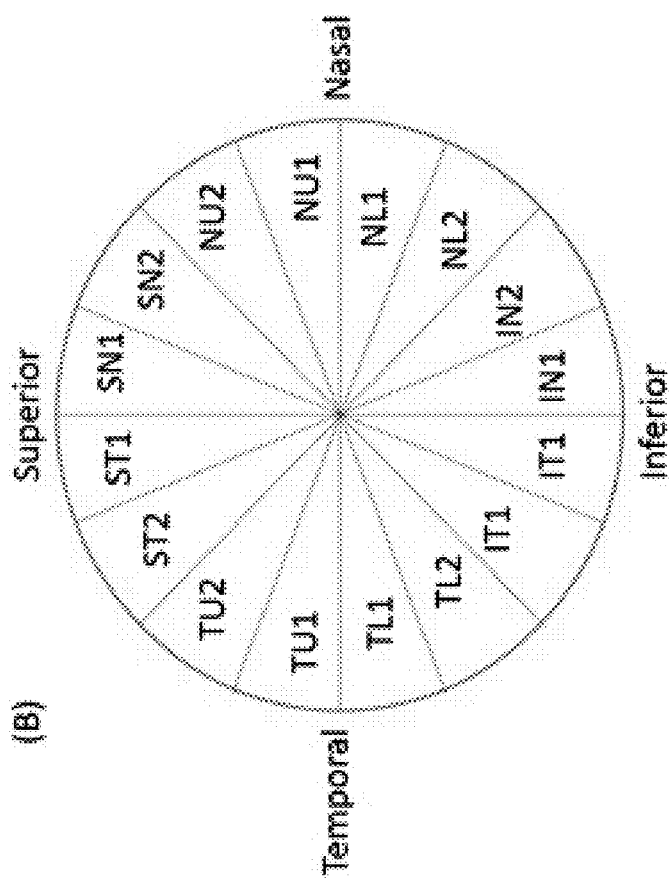
FIGS. 5A and 5B illustrate peripapillary retinal nerve fiber layer (NFL) parameters from spectral-domain OCT, in accordance with various embodiments.
Figure 5A:
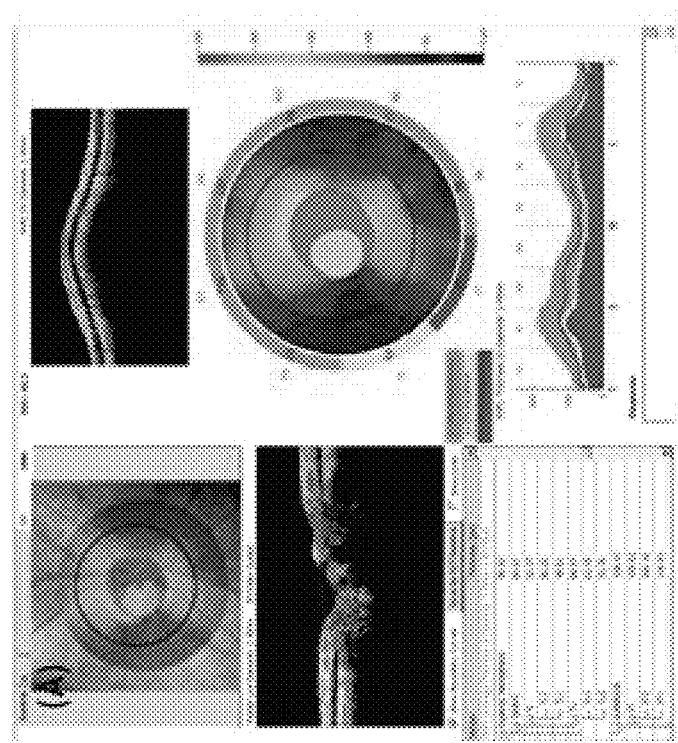

The NFL thickness profile (D=3.4 mm) was output as average values in 16 sectors, 4 quadrants, 2 hemispheres, and 1 overall circle (FIGS. 5A and 5B).

Age and Axial Length Correction

In the normal group, we found signification correlation between NFL thickness and age and axial length (p<0.001). Thus a multivariant regression was used to correct the NFL thickness. The regression is applied to each sector seperately. Based on the regression, the sector NFL thickness was corrected to reference age and axial length. The reference age was selected to 50 years to match the VF test. The reference axial length was select to the average axial length (23.6 mm) of the emmetropic (spherical equivalent refraction between −1.00 and +1.00 D) eyes in the normal group.

Floor Value of Nerve Fiber Layer Thickness

The NFL floor value refers to the residual thickness of NFL in end stage glaucoma. This thickness represents the remaining glial tissue and secondary scar tissue. In order to estimate the fraction of nerve fibers that has been lost, it is necessary to know both the reference value from a normal population, as well as the floor value from areas of severe glaucoma damage. When 100% of the nerve fibers are present, the NFL thickness should be close to the normal reference value. At the other extreme, an NFL thickness near the floor value indicates that nerve fiber survival is near 0%. To estimate the floor value, first we selected eyes with severe glaucoma according to the modified Hodapp-Parrish-Anderson criteria (VF_MD<−12 dB). In each of these eyes, the NFL sector with end-stage damage was identified as the sector with lowest NFL thickness as a percentage of the normal reference. The residual percentage from the worst sectors of these eye were then averaged to obtain the floor percentage. Finally, each sector's floor value is defined as the floor percentage times the normal reference value.

Converting Nerve Fiber Layer Thickness to a Logarithmic Decibel Scale

The following formula is used to transform NFL thickness on a μm scale to NFL loss on a dB scale:

$$NFL_{dB} = 10 \times \log 10 \left( \frac{NFL_{\mu m} - f}{N - f} \right)$$

where f is the floor; N is the normal reference (average value of healthy eyes in our normal group). This conversion formula could be applied to either overall or sector NFL thickness values.

The normal reference and floor were adjusted for age and axial length in the above formula. Multiple linear regression was performed to fit axial length and age to NFL thickness for each sectoral, quadrantile or overall average. Then the normal references were generated from the fitting equation. The floor value for NFL thickness was adjusted for axial length, but not age.

We limited the minimum value of $NFL_{dB}$ to −12.8 dB to avoid extremely negative dB values that could be obtained when NFL thickness is near the floor. The −12.8 dB minimum is equivalent to 5% above the floor value. This limit was based on the coefficient of variation of sector NFL thickness of 5% for repeat measurements in normal eyes.

Weighted Logarithm Average of Sector NFL Thickness

Figure 6C:
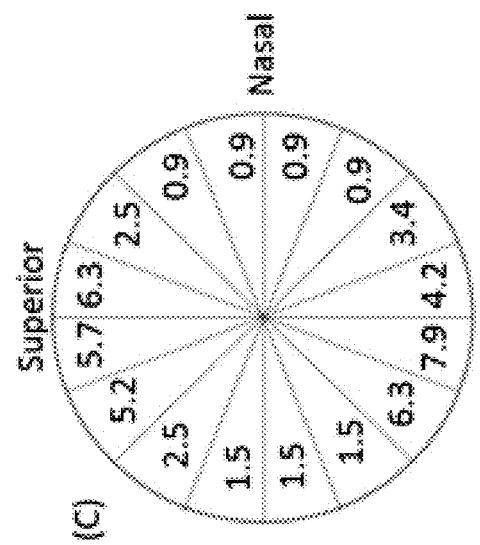
FIGS. 6A, 6B, and 6C illustrate weighting of NFL sectors used to calculate NFL mean deviation (MD), in accordance with various embodiments.
Figure 6B:
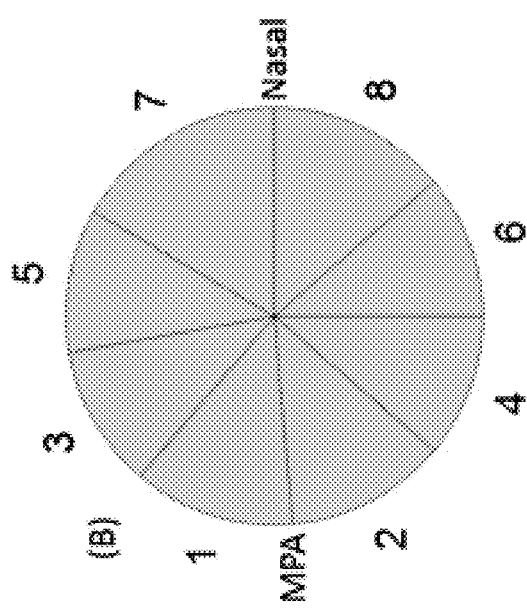
Figure 6A:
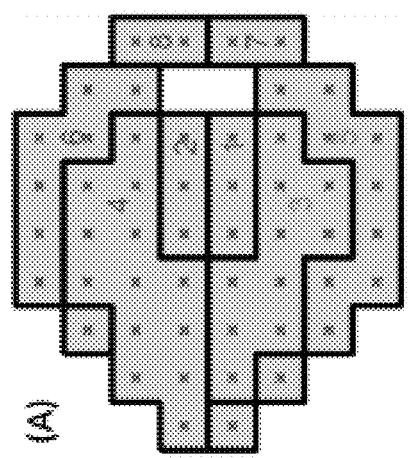

In order to simulate the VF_MD, we calculated a weighted average of sector $NFL_{dB}$. The weight is set to the VF area corresponding to NFL bundles passing through a particular peripapillary sector. To determine the weights, we used a modified Garway-Heath scheme to estimate the VF area (FIG. 6). The 6 sectors of the original Garway-Heath scheme were divided into 8 sectors by adding superior-inferior divisions. See Garway-Heath, D. F., Poinoosawmy, D., Fitzke, F. W. & Hitchings, R. A. Mapping the visual field to the optic disc in normal tension glaucoma eyes. *Ophthalmology* 107, 1809-1815 (2000); and Le, P. V. et al. Regional correlation among ganglion cell complex, nerve fiber layer, and visual field loss in glaucoma. *Invest Ophthalmol Vis Sci* 54, 4287-4295, doi:10.1167/iovs.12-11388 (2013). In the VF map, the test points are divided along the horizontal center line. In the peripapillary profile, the dividing line is the maculopapillary axis temporally and the horizontal midline nasally. The Garway-Heath sectors were originally defined at the disc rim; we extended these sector divisions outward from disc edge to the 3.4-mm diameter circle D=3.4 mm along the average trajectory of nerve fibers obtained using a published flux analysis in normal human subjects. See Tan, O., Liu, L., Liu, L. & Huang, D. Nerve Fiber Flux Analysis Using Wide-Field Swept-Source Optical Coherence Tomography. *Translational Vision Science & Technology* 7, 16, doi:10.1167/tvst.7.1.16 (2018). The weight in the 8 sectors was set to the number of VF test points in corresponding VF sector. These weights in these 8 sectors were interpolated to obtain weights for 16 evenly divided sectors (FIG. 3C). With these weights, we calculated the NFL weighted logarithm average ($NFL_{WLA}$) using the following formula:

$$NFL_{WLA} = 1/52 \Sigma_{i=1}^{16} w_i \times NFL_{dB} \quad (i)$$

where $w_i$ is the weight of a sector i; $NFL_{dB}(i)$ is the NFL loss in dB for sector 1; the number 52 is the summation of weights.

Simulation of Visual Field Mean Deviation

In order to reduce measurement noise, we averaged NFL parameters and VF_MD from 4 consecutive visits for glaucoma eyes. The first 4 consecutive visits with Spectral domain OCT scans were selected. When VF_MD was plotted against $NFL_{WLA}$, it was clear that the relationship was still significantly nonlinear. Thus a quadratic regression was used to fit the $NFL_{WLA}$ to VF_MD using all eyes from normal, PPG and PG groups. The intercept was fixed at zero with the a priori knowledge that an average normal NFL thickness profile should correspond to an average normal VF. Five-fold cross validation was used to avoid bias due to overfitting. For each fold, NFL-MD was then estimated in the validation sub-set using the corresponding fitting result. The NFL-MD obtained in 5 folds were pooled for the statistic analysis.

Statistical Analysis

The t-test was used to compare the mean values of parameters between groups.

A percentile bootstrap method were used to compare the correlation coefficients between NFL parameters and VF_MD. See Wilcox, R. R. Comparing dependent robust correlations. *Br J Math Stat Psychol* 69, 215-224, doi: 10.1111/bmsp.12069 (2016).

To assess between-visit reproducibility, the residual of linear regression over time was calculated for the 4 consecutive visits in glaucoma eyes. This was applied to the overall NFL thickness, NFL_MD, and VF_MD. The residuals are pooled by groups stratified by glaucoma severity. Glaucoma severity was staged by a modified Hodapp-Parrish-Anderson (HPA) classification system: Stage 0—PPG, Stage 1—early PG (MD>=−6 dB), Stage 2 moderate PG (−12 dB<=MD<−6 dB), and Stage 3—severe PG (MD<−12 dB). See Hodapp, E., Parrish, R. I. & Anderson, D. *Clinical decisions in glaucoma*. pp. 52-61 (The CV Mosby Co, 1993).

Intra-class correlation (ICC) was used to compare the within-visit repeatability and between-visit reproducibility of overall NFL thickness average and NFL_MD. See Tan, O. et al. Detection of macular ganglion cell loss in glaucoma by Fourier-domain optical coherence tomography. *Ophthalmology* 116, 2305-2314 e2301-2302, doi:10.1016/j.ophtha.2009.05.025 (2009). The within-visit repeatability was based on scans in baseline visits. The between-visit reproducibility was based on pairwise analysis between the baseline and the first follow-up visit.

To assess agreement, the difference between NFL_MD and VF_MD was calculated in each eye from each visit. The mean difference was averaged over the 4 consecutive visits and then averaged again in each of the 4 groups. The standard deviation was calculated by pooling the difference over the 4 consecutive visits by root mean square. Then it is pooled again in each of the three groups. Agreement between NFL_MD and VF_MD was also assessed by Bland-Altman analysis. Agreement between NFL_MD and VF_MD for glaucoma staging was assessed by the F1-score.

The diagnostic accuracy of separating PPG and PG groups from the normal group were evaluated by the areas under the receiver operating characteristic curves (AROC), and sensitivity at 95% and 99% specificity cutoffs. See Tan, O. et al. Detection of macular ganglion cell loss in glaucoma by Fourier-domain optical coherence tomography. *Ophthalmology* 116, 2305-2314 e2301-2302, doi:10.1016/j.ophtha.2009.05.025 (2009). The cutoff thresholds were based on the mean and standard deviation from normal eyes after age and axial length adjustment, assuming normal distribution. The 95%/99% specificity cutoff was set at 1.65/2.33 standard deviations (SD) below the mean of the normal group. The overall and inferior NFL thickness values had a normal distribution in the normal group according to the Kolmogorov-Smirnov normality test. VF_MD and NFL_MD had normal distributions only after transformation from dB to linear scale, therefore their diagnostic cutoff values were calculated on the linear scale and then transformed back to the dB scale.

All statistical analyses were done using MATLAB with the statistical toolbox.

Example 2—Estimating Visual Field Mean Deviation Using OCT—Angiography

1. Introduction

Glaucoma is the leading cause of irreversible blindness worldwide. Early diagnosis and monitoring with appropriate treatment are necessary to prevent visual loss which is irreversible and usually becomes symptomatic only in its late stages. Current methods of assessing glaucoma and its progression have significant limitations. The visual field (VF) directly assesses function, but the testing is subjective, time consuming, and poorly repeatable. Quantitative imaging of the peripapillary retinal nerve fiber layer (NFL) with optical coherence tomography (OCT) provides a faster, more repeatable and objective assessment in the diagnosis and monitoring glaucoma. However, NFL thickness has only moderate correlation with VF parameters, and the correlation further deteriorates in the later stages of glaucoma due to the "floor effect." Therefore, structural OCT NFL measurements perform relatively poorly in the monitoring of moderate to severe glaucoma. To further improve glaucoma monitoring, we need a new objective measure of glaucoma severity that retains good correlation with VF in the later stages of glaucoma.

Optical coherence tomography angiography (OCTA) is a noninvasive imaging modality to evaluate blood flow. OCTA parameters such as vessel density and flow index of the optic nerve head, peripapillary retina, and macula are reduced in glaucoma compared to normal participants. OCTA-derived nerve fiber layer plexus (NFLP) capillary density measurements are highly reproducible and, compared to NFL thickness, are more tightly correlated with VF parameters, even in the later stages of glaucoma. Thus, NFLP parameters may hold promise for improving glaucoma monitoring.

Although the correlation between NFLP capillary density and VF parameters is high, it is not linear. One reason is that NFLP vessel density is measured on the linear scale (% area), while VF parameters are typically represented in a logarithmic scale (e.g., dB change in retinal sensitivity). Another reason is that NFLP loss is weighted by peripapillary analytic area, while retinal sensitivity is weighted by VF area. Thus, the summary parameters for NFLP (average capillary density) and VF (mean deviation) are calculated on different scales with different weighting. We believe that the correlation between NFLP and VF could be further improved by bridging these methodological differences. To test this hypothesis, we developed a method to simulate visual fields using OCTA measurements of NFLP on a sector basis. The simulated VF is then evaluated in terms of agreement and correlation with actual VF in the glaucoma patient. Its glaucoma diagnostic accuracy and reproducibility are also assessed and compared with actual VF and NFL thickness parameters. The overall aims are to develop an optimal OCTA NFLP-based VF simulation and provide a preliminary evaluation of its potential as a new objective metric for the diagnosis, staging, and monitoring of glaucoma.

2. Methods 2.1 Study Population

This prospective observation study was performed at the Casey Eye Institute, Oregon Health & Science University (OHSU). The research protocols were approved by the Institutional Review Board at OHSU, and carried out in accordance with the tenets of the Declaration of Helsinki. Written informed consent was obtained from each participant.

All participants were part of the "Functional and Structural Optical Coherence Tomography for Glaucoma" study. The inclusion criteria for the perimetric glaucoma (PG) group were: (1) an optic disc rim defect (thinning or notching) or NFL defect visible on slit-lamp biomicroscopy; and (2) a consistent glaucomatous pattern, on both qualifying Humphrey SITA 24-2 VFs, meeting at least one of the following criteria: pattern standard deviation (PSD) outside normal limits ($p<0.05$) or glaucoma hemifield test outside normal limits. The inclusion criteria for the pre-perimetric glaucoma (PPG) group were: (1) an optic disc rim defect (thinning or notching) or NFL defect visible on slit-lamp biomicroscopy; and (2) VF not meeting the criteria for the PG group.

For the normal group, the inclusion criteria were: (1) no evidence of retinal pathology or glaucoma; (2) a normal Humphrey 24-2 visual field; (3) intraocular pressure <21 mm Hg; (4) central corneal pachymetry >500 microns; (5) no chronic ocular or systemic corticosteroid use; (6) an open angle on gonioscopy; (7) a normal appearing optic nerve head (ONH) and NFL; and (8) symmetric ONH between left and right eyes.

The exclusion criteria for both groups were: (1) best-corrected visual acuity less than 20/40; (2) age <30 or >80 years; (3) refractive error of >+3.00 D or <−7.00 D; (4) previous intraocular surgery except for an uncomplicated cataract extraction with posterior chamber intraocular lens implantation; (5) any diseases that may cause VF loss or optic disc abnormalities; or (6) inability to perform reliably on automated VF testing. One eye from each participant was scanned and analyzed. For normal eyes, the eye was randomly selected. For the PPG and PG group, the eye with the worse VF was selected.

2.2 Visual Field Testing

VF tests were performed with the Humphrey Field Analyzer II (Carl Zeiss, Inc.) set for the 24-2 threshold test, size III white stimulus, using the SITA standard algorithm. The VF test was done at baseline for all participants and then every 6 months for glaucoma participants.

2.3 Nerve Fiber Layer Plexus Capillary Density Measurement and Conversion to Decibel Scale 2.3.1 Optical Coherence Tomography A 70-kHz, 840-nm wavelength spectral-domain OCT system (Avanti, Optovue Inc.) with the AngioVue OCTA software was used.

2.3.2 Image Acquisition and Processing

The peripapillary retinal region was scanned using a 4.5×4.5-mm volumetric angiography scan centered on the optic disc. Each volume was comprised of 304 line-scan locations at which 2 consecutive B-scans were obtained. Each B-scan contained 304 A-scans. The AngioVue software used the split-spectrum amplitude-decorrelation angiograph (SSADA) algorithm, which compared the consecutive B-scans at the same location to detect flow using motion contrast. Each scan set was comprised of 2 volumetric scans: 1 vertical-priority raster and 1 horizontal-priority raster. The AngioVue software used an orthogonal registration algorithm to register the 2 raster volumes to produce a merged 3D OCT angiogram. Two sets of scans were performed within one visit. The OCT angiogram with higher signal strength index (SSI) was used in the following analysis. The OCTA scan was done at baseline for all participants and then every 6 months for glaucoma participants.

The merged volumetric angiograms were then exported for custom processing using the Center for Ophthalmic Optics & Lasers-Angiography Reading Toolkit (COOL-ART) software. The OCTA scans contained both volumetric flow (decorrelation) data as well as structural (reflectance) data. Segmentation of the retinal layers was performed by automated MATLAB programs that operate on the structural OCT data. Further manual correction of the segmentation was conducted if required. An en face angiogram of retinal nerve fiber layer plexus (NFLP) was obtained by maximum flow (decorrelation value) projection. COOL-ART removed flow projection artifacts and calculated reflectance-compensated capillary density. The vessel density (VD), defined as the percentage area occupied by the large vessels and microvasculature, was evaluated in the 4×4 mm analytic area excluding the central 2 mm diameter circle, which was manually centered on the optic disc based on the enface reflectance image. Arterioles and venules (larger vessels) were automatically identified by thresholding the en face mean projection of OCT reflectance within the all-plexus slab. After these larger vessels were excluded, the remaining angiogram was used to compute capillary density.

2.3.3 Nerve Fiber Layer Plexus Sector Division

Figure 7:
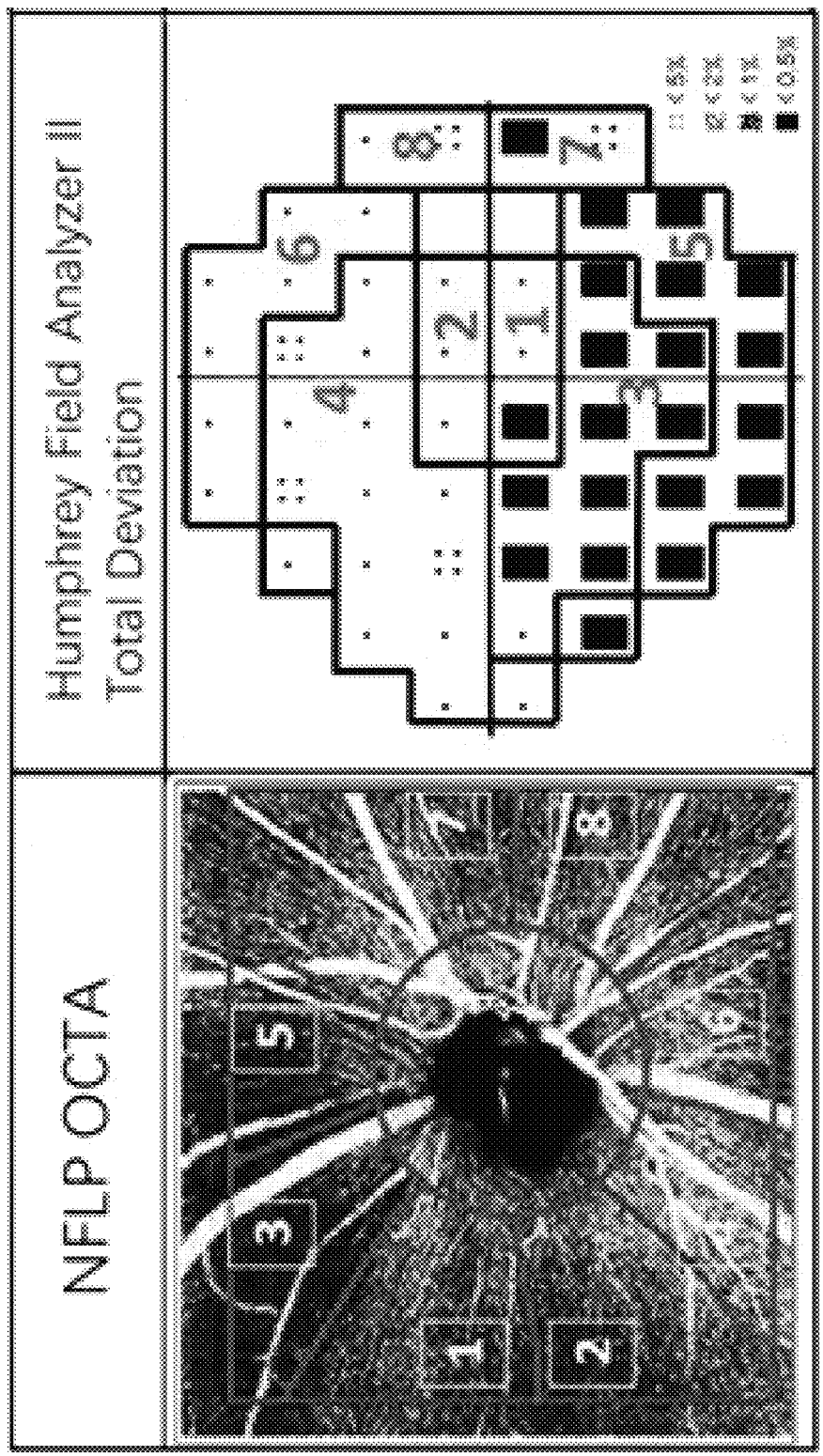
FIG. 7 illustrates an en face OCT angiogram of the nerve fiber layer plexus (NFLP) and the visual field (VF) map for a perimetric glaucomatous eye divided into 8 corresponding sectors according to a modified Garway-Heath scheme, in accordance with various embodiments.

The en face OCTA of the NFLP and the VF total deviation map were divided into 8 corresponding sectors according to a modified Garway-Heath scheme (FIG. 7). The original Garway-Heath scheme divided the disc rim into 6 sectors. See Le P V, Tan O, Chopra V, et al. Regional correlation among ganglion cell complex, nerve fiber layer, and visual field loss in glaucoma. Invest Ophthalmol Vis Sci 2013; 54:4287-95; and Garway-Heath D F, Poinoosawmy D, Fitzke F W, Hitchings R A. Mapping the visual field to the optic disc in normal tension glaucoma eyes. Ophthalmology 2000; 107:1809-15. We added horizontal dividing lines to the original nasal and temporal sectors to increase the total number of sectors to 8. The sector boundaries were extended outward along nerve fiber trajectories obtained from structural OCT nerve fiber flux analysis. See Tan O, Liu L, Liu L, Huang D. Nerve Fiber Flux Analysis Using Wide-Field Swept-Source Optical Coherence Tomography. Translational Vision Science & Technology 2018; 7:16.

2.3.4 Floor Value of Nerve Fiber Layer Plexus Capillary Density

Figure 8B:
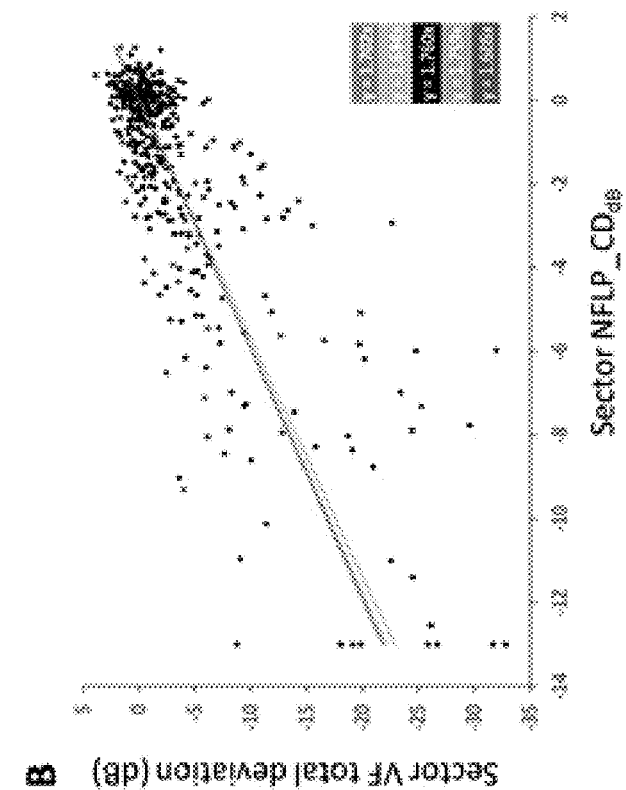
FIG. 8B is a plot of sector visual field total deviation and sector RNFLP_CD on a dB scale in accordance with various embodiments, which shows a linear relationship. Five linear regression results are shown (color-coded regression formulas on right) according to the 5-fold cross-validation method. The linear fit was used for VF simulation after placing a lower limit of −13.0 dB on the $NFLP\_CD_{dB}$ value.
Figure 8A:
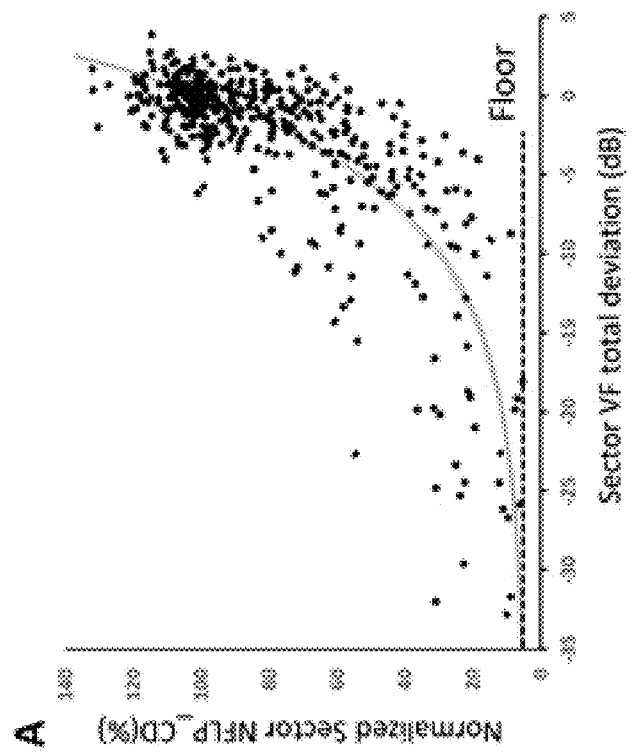
FIG. 8A is a plot of normalized sector NFLP capillary density (NFLP_CD) (%) and sector visual field total deviation (dB) in accordance with various embodiments, which shows an exponential decay relationship with a floor value of 7.0%.

The NFLP capillary density (NFLP_CD) has a nonlinear relationship with VF—the slope is relatively steep in early stages of glaucoma and flattens in later stages. Our mathematical model linking NFLP_CD and VF includes an NFLP_CD floor value, which represents the residual NFLP capillaries in end-stage glaucoma. The floor value is proportional to the normal values for each sector. This common floor fraction is estimated using the normalized sector NFLP_CD, which is defined as the sector NFLP_CD divided by the reference NFLP_CD of the corresponding sector. The reference NFLP_CD was obtained by averaging measurements in the normal group. The normalized NFLP_CD values of all sector measurements in the glaucoma group were pooled (FIG. 8A). The first percentile cut off point of the pooled distribution was used as the residual fraction. Finally, each sector's floor value is defined as the floor fraction times the normal reference value.

2.3.5 Converting Sector Nerve Fiber Layer Plexus Capillary Density to a Decibel Scale The following formula is used to transform NFLP_CD on a % area scale to NFLP_CD loss on a dB scale.

$$\text{Sector NFLP\_CD}_{dB} = 10 \times \log10\left(\frac{\text{Sector NFLP\_CD}_{\%area} - f}{N - f}\right)$$

where f is the floor, N is the normal reference value (average value of healthy eyes in our normal group).

We limited the minimum value of sector $\text{NFLP\_CD}_{dB}$ to −13 dB to avoid extremely negative dB values that could be obtained when NFLP_CD is near the floor. The −13 dB limit was based on the coefficient of variation of sector NFLP_CD of 5.0% for repeat measurements in normal eyes.

2.3.6 Simulating Sector Visual Field Deviation

A linear regression was used to fit the sector $\text{NFLP\_CD}_{dB}$ to VF sector deviation.

Data from both normal and glaucomatous eyes were used. Measurements from sector 1 to sector 6 were pooled. We did not use data from sector 7 and 8 in the regression analysis because these sectors contained only 2 VF test points each and had relatively poor reproducibility. The intercept was fixed at zero with the a priori knowledge that an average normal $\text{NFLP\_CD}_{dB}$ should correspond to an average normal VF. Using the regression formula, the sector $\text{NFLP\_CD}_{dB}$ was converted to simulated sector visual field deviation (NFLP_simVF) with the unit in the decibel scale. A color-coded NFLP_simVF total deviation map with 8 sectors was generated by the sector NFLP_simVF.

2.4 Calculating the Mean Deviation of the Simulated Visual Field

The sector NFLP_simVF values were weighted and averaged to generate the NFLP simulated visual field mean deviation (NFLP_MD) with the unit in the decibel (dB) scale. The weight for each sector is proportional to the number of VF test points within the sector (FIG. 7). The weights in the 8 sectors were set proportional to the number of VF test points in the corresponding VF sector.

$$\text{NFLP\_MD} = \Sigma_{i=1}^{8} w_i \times \text{NFLP\_simVF} \quad (i)$$

The $w_i$ is the weight of sector i. The weights of sectors 1 to 8 are 0.06, 0.06, 0.19, 0.25, 0.21, 0.15, 0.04, and 0.04. They sum to 1.

In order to reduce measurement noise, we averaged OCT, OCTA, and VF parameters from 2 visits 6 months apart for the glaucoma eyes.

2.5 Structural OCT Analysis

Peripapillary NFL thickness was measured from the Avanti's ONH structural OCT scan. The ONH scan pattern consists of concentric circular (1.3-4.9 mm diameter) scans centered on the optic disc. In post processing, the ONH scan was automatically registered with a baseline three-dimensional disc scan to provide the disc margin information. The NFL thickness profile at a diameter of 3.4 mm was resampled on the NFL thickness map, then re-centered to the detected optic disc center. The result for each participant was the average value of two sets of images obtained at one visit.

2.6 Five-Fold Cross Validation

The participants were each randomly divided into 5 subsets with equal numbers in each disease severity classification. While one subset was taken as a test set, the other four subsets were used to calculate the regression formula for simulating the VF. This provided five sets of regression results that were used to convert sector $\text{NFLP\_CD}_{dB}$ to the simulated sector visual field deviation (NFLP_simVF).

2.7 Image Quality Control and Statistical Analysis

Image quality was assessed for all OCTA scans. Poor quality scans with SSI below 55, or registered image sets with residual motion artifacts (obvious break in the pattern of large vessels) were excluded from analysis. Between-visit reproducibility was assessed by the pooled standard deviation (Pooled SD) and the intraclass correlation coefficient (ICC). Agreement between NFLP_MD and VF_MD was also assessed by Bland-Altman analysis. The Student's t test was used to compare normal and glaucoma groups. The area under the receiver operating characteristic curve (AROC), sensitivity, and specificity were used to evaluate diagnostic accuracy. The estimated sensitivities for fixed specificities were calculated by the method of Zhou et al. See Zhou X-H, McClish DK, Obuchowski N A. Statistical methods in diagnostic medicine: John Wiley & Sons, 2009. McNemar test was used to compare these sensitivities. To investigate the location correspondence of NFLP_simVF and actual VF, the worst sector was defined as the sector having the lowest average value and its location was compared between NLFP_simVF and actual VF. The statistical significance was assumed at P<0.05. All statistical analyses were performed with SPSS20.0 (SPSS Inc., Chicago, Ill.) and MedCalc 10.1.3.0 (MedCalc Software, Ostend, Belgium).

3. Results 3.1 Study Population

Thirty-one normal eyes from 31 normal participants and 39 glaucomatous eyes from 39 glaucoma participants were analyzed in this study. In the glaucoma group, 1 participant had pre-perimetric glaucoma, 23 had early glaucoma (MD>−6 dB), 10 had moderate glaucoma (MD between −6 and −12 dB), and 5 had severe glaucoma (MD between −12 and −20 dB), according to the modified Hodapp-Parrish-Anderson classification system. See Hodapp E PRI, Anderson D R. Clinical decisions in glaucoma: St Louis: The CV Mosby Co, 1993. pp. 52-61. There was no statistically significant difference between the normal and glaucoma groups for age, intraocular pressure, and systolic/diastolic blood pressures (Table 7). The glaucoma group had worse VF, thinner NFL, and lower NFLP_CD than the normal control group, as expected (Table 7).

The normal population SD for NFLP_MD was 0.5 dB, which was significantly (P<0.001) tighter than 1.3 dB for the normal population SD for VF_MD (Table 7). The differences between glaucomatous eyes and normal eyes were similar for the two parameters. Thus, the tighter normative distribution for NFLP_MD may provide an advantage for distinguishing glaucomatous eyes from normal eyes.

−22.8 dB, confirming that these sectors have end-stage glaucoma damage. This floor fraction (FIG. 8A) was used in converting NFLP_CD to a dB scale as described in the methods section.

For the purpose of 5-fold cross-validation, the participants were each randomly divided into 5 subsets with equal numbers in each disease severity classification. This provided 5 sets of regression formulas that were used to convert sector NFLP_CD$_{dB}$ to simulated sector visual field deviation (NFLP_simVF). Sector NFLP_simVF=slope*sector NFLP_CD$_{dB}$, slope=1.718±0.038 (Mean±Standard Deviation); and $R^2$ ranged from 0.626 to 0.659 for formulas 1 to 5 (FIG. 8B). There was no significant difference in regression fit parameters if the sectors were analyzed separately, thus the pooled regression approach was permissible. A lower limit of −13.0 dB was placed on NFLP_CD$_{dB}$ value, corresponding to the coefficient of variation of sector NFLP_CD of 5.0%, for repeat measurements in normal eyes. The equivalent lower limits on NFLP_simVF ranged from −21.9 dB to −22.9 dB for formula 1 to 5. This limit prevents vessel density measurement noise from being excessively amplified when NFLP_CD values are close to the floor.

The sector NFLP_simVF values were averaged with weights proportional to VF area to generate the global simulated visual field mean deviation (NFLP_MD) as mentioned in Methods Section 2.4.

3.3 Agreement and Reproducibility of OCTA and VF Parameters

The NFLP-based VF simulation had a better between-visit reproducibility than actual visual fields on both sector-wise (Table 8) and global (Table 8) analyses. These differ-

TABLE 7

Participants' Characteristics

| Parameter | | Normal | Glaucoma | Difference (P value) |
|---|---|---|---|---|
| Participants, n | | 31 | 39 | |
| Eyes, n | | 31 | 39 | |
| Age (Years) | | 65 ± 9 | 65 ± 10 | 0 (0.853) |
| Intraocular Pressure (mm Hg) | | 14.6 ± 3.6 | 15.3 ± 2.7 | 0.7 (0.767) |
| Diastolic Blood Pressure (mm Hg) | | 76.0 ± 15.0 | 77.5 ± 11.2 | 1.5 (0.697) |
| Systolic Blood Pressure (mm Hg) | | 120.9 ± 23.2 | 124.9 ± 14.7 | 4.0 (0.385) |
| Visual Field | MD (dB) | −0.1 ± 1.3 | −6.0 ± 4.4 | −5.9 (<0.001) |
| | PSD (dB) | 1.0 ± 0.2 | 6.4 ± 3.9 | 5.4 (<0.001) |
| Structural OCT Thickness Measuremen | NFL (µm) | 98.8 ± 7.6 | 75.8 ± 12.3 | −23.0 (<0.001) |
| OCT Angiography Measurements | Overall NFLP_CD (% area) | 69.2 ± 4.9 | 45.3 ± 12.6 | −23.9 (<0.001) |
| | NFLP_MD (dB) | −0.1 ± 0.5 | −5.6 ± 3.2 | −5.5 (<0.001) |

Group mean ± standard deviation are shown.
VF_MD = visual field mean deviation;
NFLP_MD = retina nerve fiber layer plexus mean deviation (simulated visual field mean deviation);
NFLP_CD = retina nerve fiber layer plexus capillary density;
NFL = nerve fiber layer 3.2 Floor Values and Visual Field Simulation The normative reference values of NFLP_CD in sectors 1 to 8 were 67.5, 61.7, 87.2, 88.7, 81.2, 74.8, 66.6 and 54.8% area, respectively. The floor fraction was 7.0%, representing the residual capillary density in sectors with the most significant perfusion loss (1 percentile cutoff). The average VF sector total deviation in the sectors below the cutoff was ences were statistically significant for sector and mean deviation values for the pooled SD (P<0.02). But, the differences in ICC were not statistically significant. Since the reproducibility was calculated from visits 6 months apart, we examined whether disease progression in the glaucoma group could have biased the pooled SD values. In the glaucoma group, the average difference between the baseline NFLP_MD and repeat measurement 6 months later was 0.08 dB, which was small compared to the within-visit repeatability of 0.69 dB and the between-visit reproducibility of 0.63 dB (Pooled SD). The average difference between the baseline VF_MD and repeat measurement 6 months later was 0.16 dB, which is small compared to the between-visit reproducibility of 1.03 dB (Pooled SD). Therefore, we concluded that disease progression did not significantly affect the calculation of the reproducibility of NFLP_MD and VF_MD.

The sector NFLP-based VF simulation and actual VF had fair agreement on a sector basis (Table 8) and good agreement on a mean deviation basis (Table 9).

Figure 9:
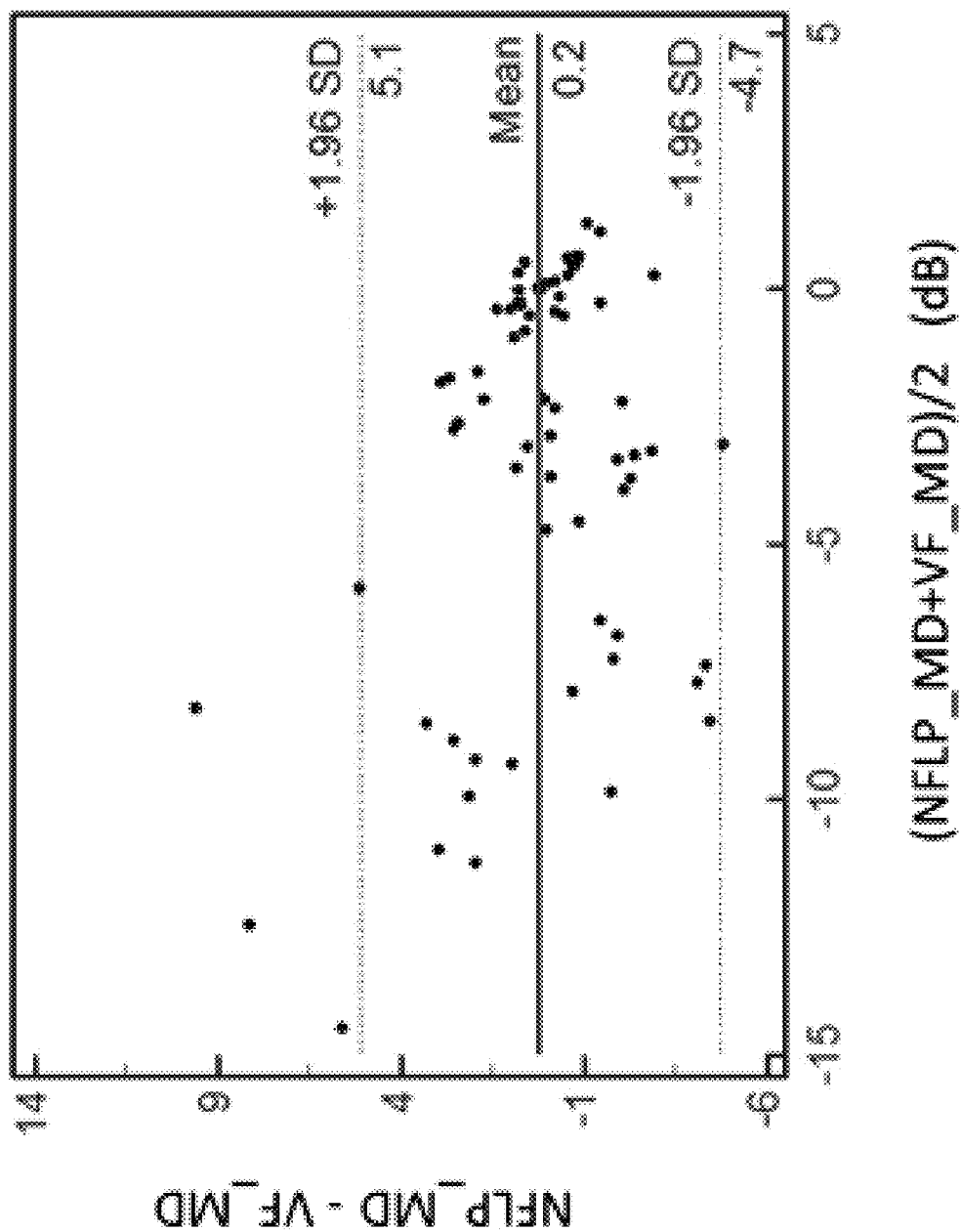
FIG. 9 illustrates Bland-Altman analysis of the agreement between nerve fiber layer plexus mean deviation (NFLP_MD) and visual field mean deviation (VF_MD), in accordance with various embodiments. Data from the normal and glaucoma groups are combined.

The difference analysis (Table 10) and Bland-Altman analysis (FIG. 9) showed that the agreement between NFLP_MD and VF_MD was good in early and moderate glaucoma stages. However, in the advanced glaucoma stage, NFLP_MD tended to under-estimate the severity of actual visual field. Although the difference between NFLP_MD and VF_MD in the severe glaucoma group was not statistically significant (p=0.06) due to the small sample size, the magnitude of the difference (5.8 dB) was clinically significant. The spread between NFLP_MD and VF_MD increased with increasing glaucoma severity. One possible explanation for the discrepancy between NFLP_MD and VF_MD is cataract severity. Therefore, we examined cataract severity and best corrected visual acuity (BCVA) in the different stages of glaucoma (Table 10). No significant differences in cataract severity or BCVA were found between glaucoma stages.

The Pearson correlation between NFLP_MD and VF_MD was significantly (p=0.001) higher than that between NFLP_CD (in % area scale) and VF_MD (FIG. 10). This shows that our method of VF simulation improved correlation with actual VF. The correlation appears to be linear in all stages of the disease. However, in the moderate to severe stage eyes, there were several outliers in which VF_MD indicated more severe damage than NFLP_MD.

TABLE 8

Sectorwise Agreement and Reproducibility for Visual Field & Optical Coherence Tomographic Angiography

|  | NFLP_simVF v. VF‡ | VF v. VF* | NFLP_simVF v. NFLP_simVF* |
|---|---|---|---|
| Intraclass Correlation Coefficient (95% Confidence Interval) | 0.745 (0.706 to 0.780) | 0.931 (0.916 to 0.944) | 0.945 (0.937 to 0.960) |
| Pooled Standard Deviation (dB) | 2.63 | 1.69 | 1.20 |

The 8 Garway-Heath sectors were pooled for this analysis.

‡The agreement between sector visual field (VF) deviation (average total deviation value of test points within each sector) and retina nerve fiber layer plexus-based simulated visual field sector values (NFLP_simVF) measured on the same visit were assessed. Both normal and glaucoma groups were used in this analysis.

*The reproducibility of VF and NFLP_simVF sector values were measured in the glaucoma group using data from 2 visits 6 months apart.

TABLE 9

Global Agreement and Reproducibility for Visual Field & Optical Coherence Tomographic Angiography

|  | NFLP_MD v. VF_MD‡ | VF_MD v. VF_MD* | NFLP_MD v. NFLP MD* |
|---|---|---|---|
| Intraclass Correlation Coefficient (95% Confidence Interval) | 0.808 (0.709 to 0.876) | 0.946 (0.900 to 0.971) | 0.954 (0.910 to 0.977) |
| Pooled Standard Deviation (dB) | 1.78 | 1.03 | 0.63 |

‡The agreement between visual field mean deviation (VF_MD) and retina nerve fiber layer plexus mean deviation (NFLP_MD) measured on the same visit were assessed. Both normal and glaucoma groups were used in this analysis.
*The between-visit reproducibility of VF_MD and NFLP_MD were measured in the glaucoma group using data from 2 visits 6 months apart.

TABLE 10

Visual Field, Optical Coherence Tomographic Angiography, and Clinical

| Parameter | | | | |
|---|---|---|---|---|
|  | Normal | PPG + Early PG | Moderate PG | Severe PG |
|  | # of Subjects in Group | | | |
|  | 31 | 24 | 10 | 5 |
| VF_MD (dB) | −0.1 ± 1.3 | −3.1 ± 1.6 | −8.9 ± 1.7 | −14.3 ± 2.4 |
| NFLP_MD (dB) | −0.1 ± 0.5 | −4.0 ± 2.5 | −8.0 ± 2.1 | −8.4 ± 3.0 |
| NFLP_MD − VF_MD (dB) | 0.1 ± 1.2 | −0.9 ± 2.0 | 0.9 ± 2.9 | 5.8 ± 3.2 |
| Cataract (0-4) | 0.8 ± 0.9 | 1.1 ± 1.1 | 1.9 ± 0.7 | 1.4 ± 0.7 |
| BCVA (LogMAR) | 0.0 ± 0.10 | 0.0 ± 0.10 | 0.06 ± 0.16 | 0.04 ± 0.09 |

Parameters Stratified by Glaucoma Severity

Group mean ± standard deviation are shown.

VF_MD = visual field mean deviation;

NFLP_MD = retina nerve fiber layer plexus mean deviation (simulated visual field mean deviation);

BCVA = best corrected visual acuity;

logMAR = logarithm of minimum angle of resolution;

PPG = pre-perimetric glaucoma;

PG = perimetric glaucoma.

3.4 Diagnostic Accuracy of OCTA, Simulated VF and Actual VF Parameters

The diagnostic accuracies of NFLP_MD, NFLP_CD, VF_MD and NFL thickness were compared (Table 11). For the discrimination between normal and glaucoma groups, NFLP_MD had the highest AROC. But the AROC advantage was not statistically significant. When the specificity was fixed at 99%, NFLP_MD had a significantly better sensitivity than VF_MD (P<0.001) and overall NFL thickness (P=0.03).

TABLE 11

Diagnostic Accuracy of Optical Coherence Tomographic Angiography and Visual Field Parameters

|  | NFLP_MD | NFLP_CD | VF_MD | NFL thickness |
|---|---|---|---|---|
| AROC | 0.975 | 0.964 | 0.954 | 0.921 |
| Sensitivity at 99% Specificity | 97.4% | 87.2% | 66.7% | 82.1% |

AROC = The area under the receiver operating characteristic curve;
VF_MD = visual field mean deviation;
NFLP_MD = retina nerve fiber layer plexus mean deviation (simulated visual field mean deviation);
NFLP_CD = nerve fiber layer plexus capillary density;
NFL = retinal nerve fiber layer.

3.5 Location Correspondence of Nerve Fiber Layer Plexus Simulated VF and Actual VF Comparing NFLP_simVF total deviation map and actual VF map (average sector total deviation) in 38 perimetric glaucomatous eyes, the worst sector was in the same or neighbor location in the same hemisphere 97% of the time. In 22 (58%) of these eyes, the worst sector of NFLP_simVF and actual VF were in the same location. In 15 (39%) perimetric glaucomatous eyes, the worst sectors were in adjacent locations in the same hemisphere.

3.6 Examples of Simulated and Actual Visual Fields

Figure 11:
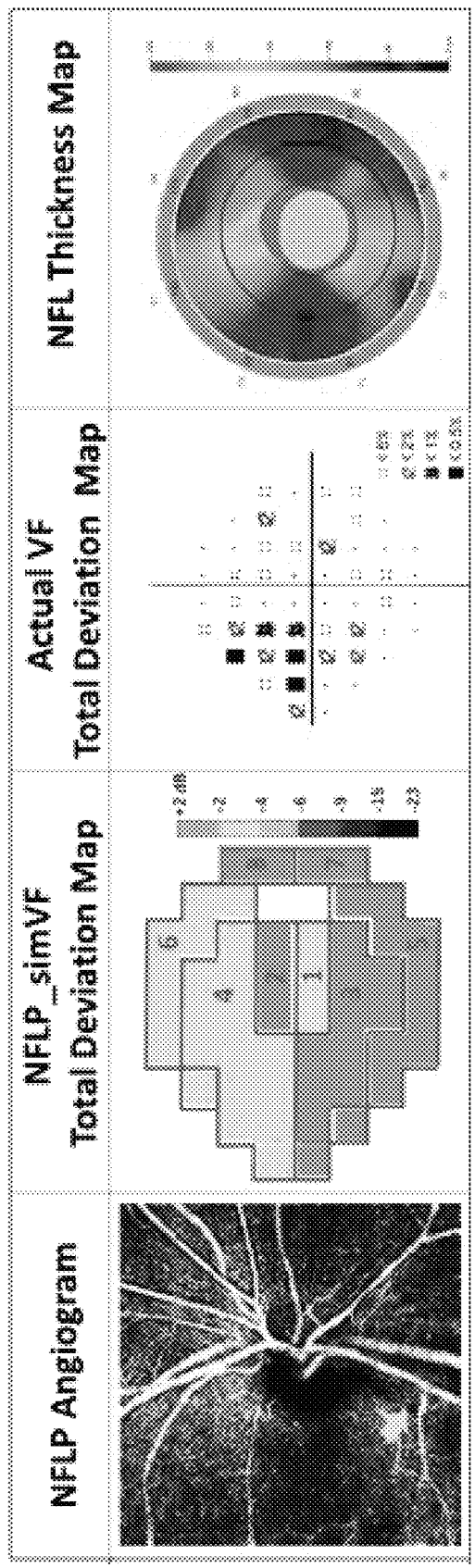
FIG. 11 illustrates an NFLP angiogram, a nerve fiber layer plexus simulated visual field (NFLP_simVF) total deviation map, an actual VF total deviation map, and an NFL thickness map for an early perimetric glaucoma eye with −3.4 dB VF_MD showing how the OCTA parameter can detect glaucoma earlier than structural OCT, in accordance with various embodiments. The NFLP angiogram showed an infratemporal bundle of capillary dropout (arrow). Both the NFLP_CD (51.1%) and NFLP_MD (−1.5 dB) were abnormally low (below 99% specificity cutoff). The simulated VF (NFLP_simVF) shows defects in sectors 1, 4, and 6 in agreement with the actual VF. The NFL thickness were within normal limits (95% specificity cutoff) for overall (106 µm) and sector values.
Figure 12:
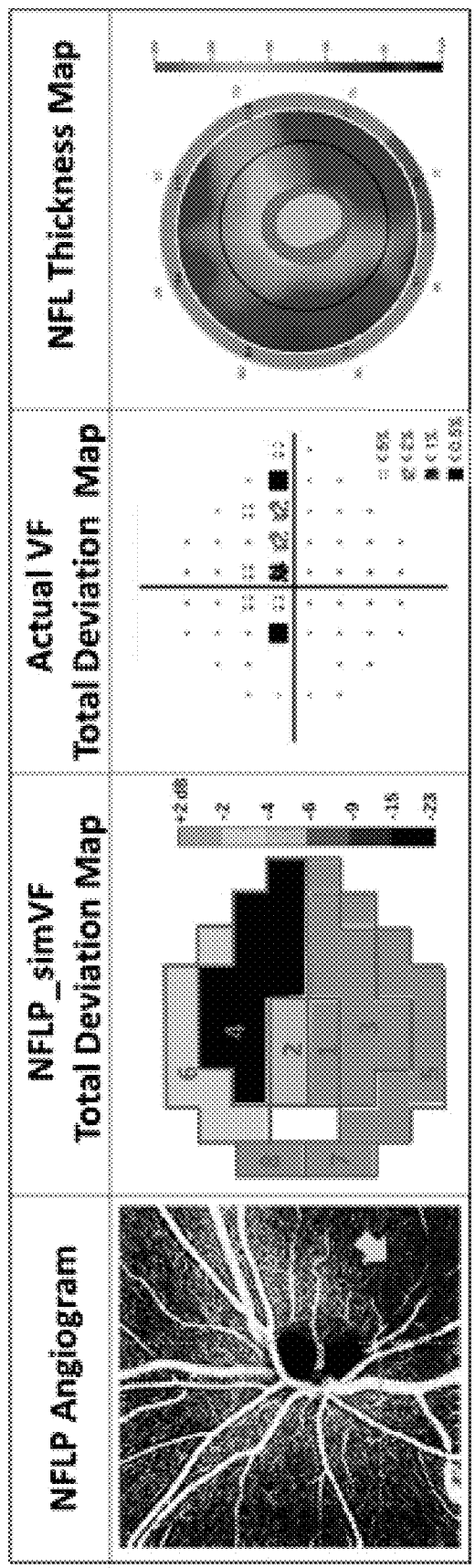
FIG. 12 illustrates an NFLP angiogram, a nerve fiber layer plexus simulated visual field (NFLP_simVF) total deviation map, an actual VF total deviation map, and an NFL thickness map for an early perimetric glaucoma with −0.7 dB VF_MD, in accordance with various embodiments. The NFLP_simVF showed more severe glaucoma damage relative to the actual VF. The NFLP angiogram showed an inferotemporal area of capillary dropout (arrow). In the NFLP_simVF map, sector 2 showed moderate defect in agreement with the actual VF, whereas in sector 4 the NFLP_simVF defect was more advanced than that on the actual VF. The retinal nerve fiber layer (NFL) thickness was thinnest in the inferotemporal (IT) sector, matching the location of the worst NFLP defect. The NFLP_MD of this case was −5.4 dB, significantly worse than the VF_MD.
Figure 13:
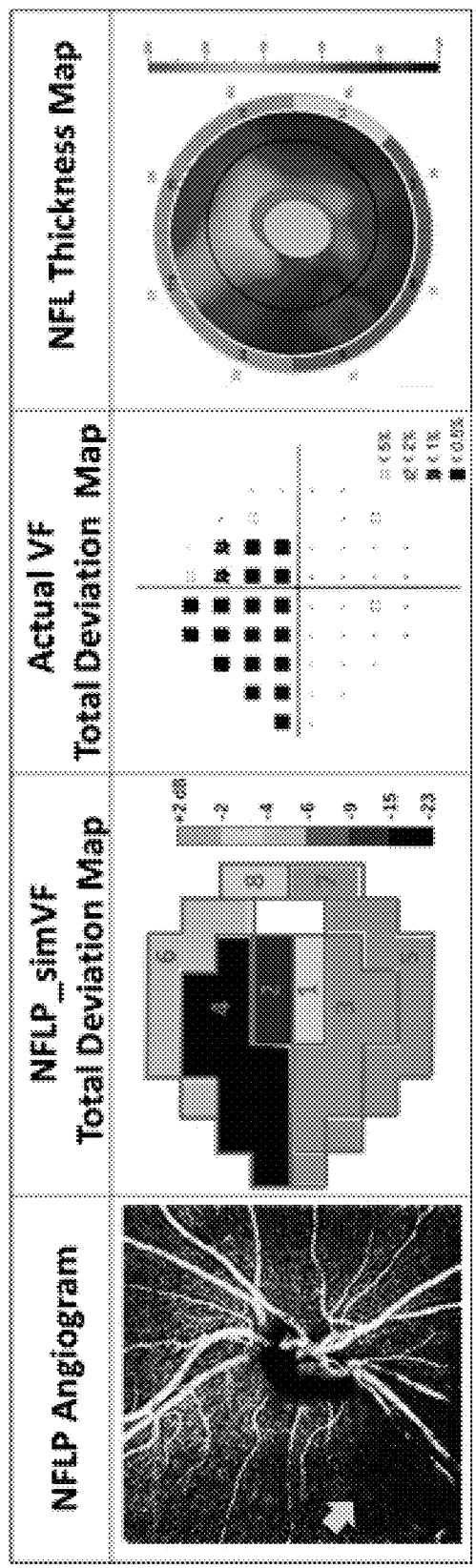
FIG. 13 illustrates an NFLP angiogram, a nerve fiber layer plexus simulated visual field (NFLP_simVF) total deviation map, an actual VF total deviation map, and an NFL thickness map for a moderate glaucoma eye with −7.5 dB visual field mean deviation (VF_MD), in accordance with various embodiments. The NFLP_simVF agreed well with the actual VF. The NFLP angiogram showed an inferior and temporal capillary dropout (arrow). In the NFLP_simVF total deviation map, sector 2, 4, and 6 had moderate to advanced defects matching the actual visual field (VF). The retinal nerve fiber layer (NFL) thickness was abnormally thin in all inferior sectors, matching the location of the NFLP defects. The NFLP_MD of this case was −8.2 dB, agreeing well with the actual VF_MD.
Figure 14:
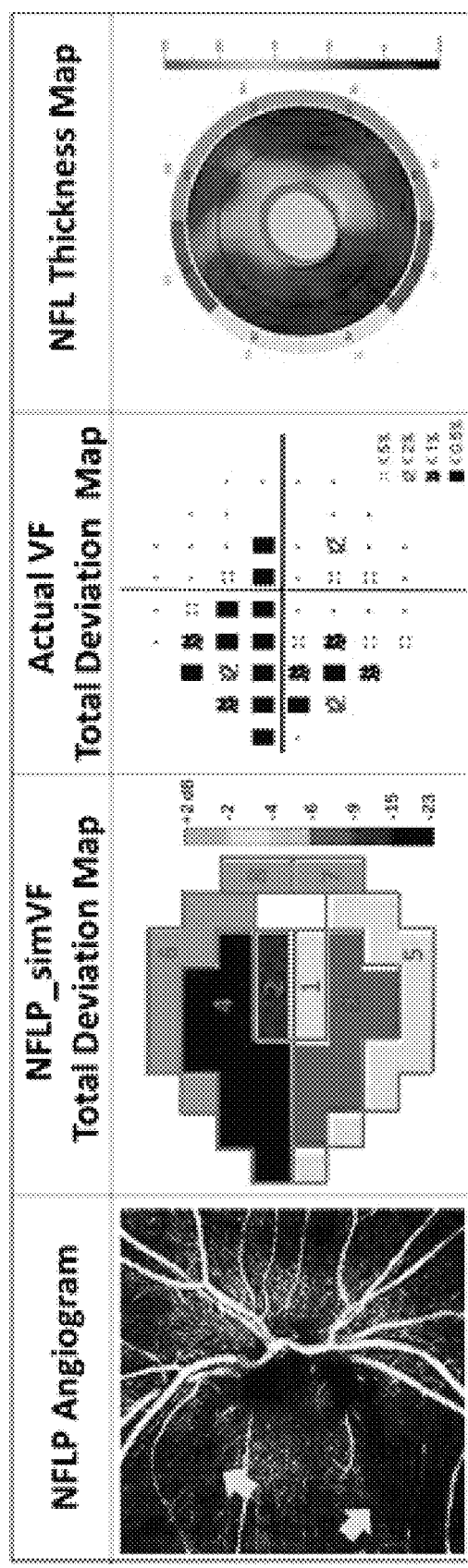
FIG. 14 illustrates an NFLP angiogram, a nerve fiber layer plexus simulated visual field (NFLP_simVF) total deviation map, an actual VF total deviation map, and an NFL thickness map for a moderate glaucoma with −6.5 dB visual field mean deviation (VF_MD), in accordance with various embodiments. The NFLP_simVF agreed well with the actual VF. The NFLP angiogram showed inferotemporal and superotemporal areas of capillary dropout (arrow). In the NFLP_simVF total deviation map, sector 2, 3 and 4 had moderate to advanced defects matching the actual visual field (VF). The retinal nerve fiber layer (NFL) thickness was abnormally thin in inferotemporal, superotemporal, and temporal sectors, matching the locations of the NFLP defects. The NFLP_MD of this case was −7.8 dB, agreeing well with the actual VF_MD.
Figure 15:
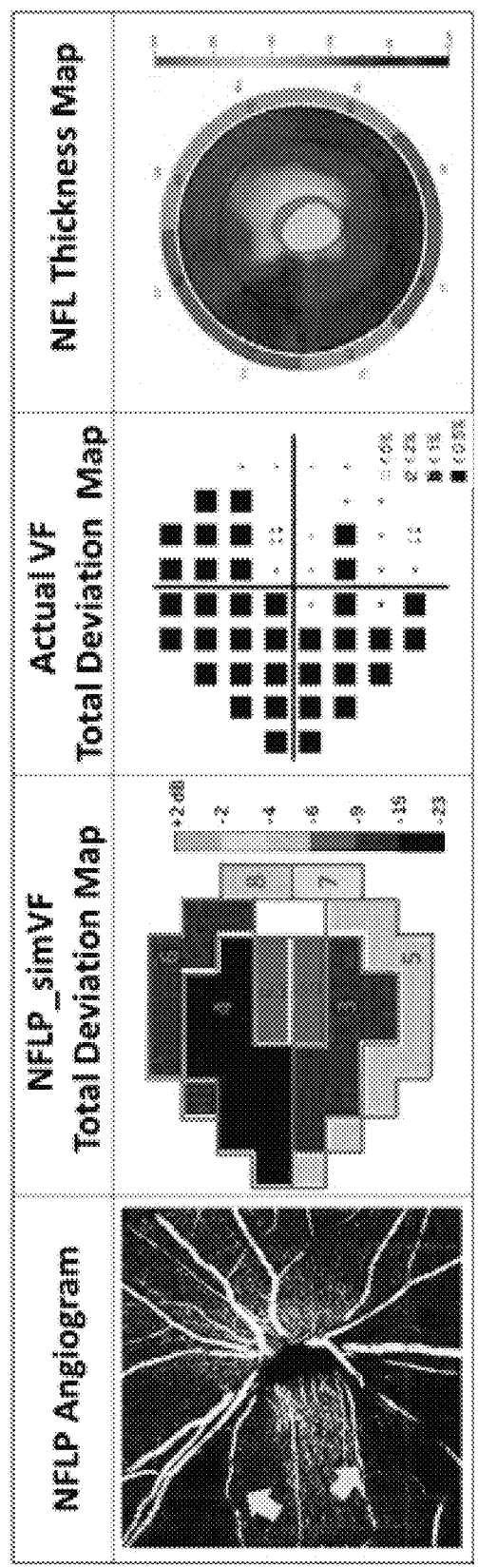
FIG. 15 illustrates an NFLP angiogram, a nerve fiber layer simulated visual field (NFLP_simVF) total deviation map, an actual VF total deviation map, and an NFL thickness map for an advanced glaucoma with −17.3 dB VF_MD, in accordance with various embodiments. The NFLP_simVF showed less severe glaucoma damage relative to the actual VF. The NFLP angiogram showed inferior and superotemporal areas of capillary dropout (arrow). In the NFLP_simVF map, sector 3, 4 and 6 showed advanced defects in agreement with the actual VF, whereas in sector 5 the NFLP_simVF defect was less severe than that on the actual VF. The retinal NFL thickness was abnormally thin in the inferior and superotemporal sectors, matching the location of the NFLP defects. The NFLP_MD of this case was −11.7 dB, significantly better than the VF_MD.

Several examples are shown to give insight on the performance NFLP_simVF. FIG. 11 demonstrates that NFLP_simVF based on OCTA could detect glaucoma earlier than structural OCT NFL thickness measurement. FIG. 12 shows a case of early glaucoma in which NFLP_simVF agreed with VF in the locations of glaucoma damage, but demonstrated greater severity. FIGS. 13 and 14 are both moderate glaucoma cases in which NFLP_simVF, VF, and NFL thickness all agreed well on the locations and severity of glaucoma damage. FIG. 15 shows an advanced glaucoma case where the NFLP_simVF pattern agreed well with the VF map, but the NFLP_MD underestimated glaucoma severity compared to VF_MD. Generally, the color-coded NFLP_simVF maps identified glaucoma damage in the same sectors as VF, but the severity of damage did not always correspond.

4. Discussion

Visual field is the standard clinical test to evaluate glaucoma progression. However, the poor reproducibility of visual fields means that many tests over long periods of time are needed to reliably detect significant progression and determine its rate. According to one analysis, a glaucomatous eye experiencing −1 dB/year of rapid VF_MD loss would require 9 tests over 4 years to have a 90% chance of confirming statistically significant (p<0.05) trend of worsening. An objectively measured surrogate for VF that has better reproducibility could allow earlier detection of rapid glaucoma progression and more timely modification of treatment that could prevent vision loss. Structural OCT measurements have been used to predict VF test results. But to the best of our knowledge, this is the first investigation into the use of OCTA measurement for VF simulation. The correlation between OCTA and VF parameters tends to be better than the correlation between structural OCT and VF, especially in the moderate and severe stages of glaucoma. Therefore OCTA could potentially be a better input for VF simulation for the purpose of monitoring glaucoma progression in the later stages.

Converting OCTA perfusion measurements as a functional equivalent serves several purposes in terms of clinical interpretation. First, information on the location and severity of visual loss is more closely related to the impact on the patient's visual function and quality of life. Second, measuring the rate of glaucoma progression in a dB scale VF equivalent is more familiar to the clinician and better reflects the impact of glaucoma on visual function. On the linear scale customary for OCT and OCTA measurements (e.g. NFL thickness in μm or capillary density in % area), the progression of glaucoma appears very rapid in the early stages and very slow in the later stages. This distorted perspective makes it difficult to assess the speed of disease progression in a clinically appropriate fashion. As illustrated by this hypothetical comparison: An early glaucoma eye with 1 million retinal nerve fibers could afford to lose 50,000 fibers per year, which constitutes a −5% or −0.22 dB change; but a severe glaucoma eye with 100,000 nerve fibers left could not afford to lose the same number of fibers, which would constitute a −50% or −3 dB change. The logarithmic dB scale offers a more appropriate perspective to compare the rate of disease progression across all stages. Therefore converting all types of glaucoma assessment, whether structure, perfusion, or retinal sensitivity to a common dB scale would facilitate a better illustration of the speed of glaucoma disease progression.

The first step in converting NFLP_CD to the dB-scale VF equivalent is determining the floor value representing the residual perfusion that remains after nearly complete loss of retinal sensitivity. The second step is a regression operation to establish the relationship between dB-scale NFLP_CD and VF retinal sensitivity (total deviation). We had to pool all sectors together (except sector 7 and 8) to obtain a large enough sample to perform these steps. The pooling was also necessary because almost all severe glaucoma damage occurred in sectors 3 and 4 (arcuate sectors), so that there is insufficient information in the other sectors for floor and regression calculations. The results justified this approach— the correlation between pooled normalized logarithmic sector NFLP_CD and VF was high ($r^2$=0.622) and highly linear. In addition, there was no significant difference in fit parameters if the sectors were separately analyzed. The floor fraction of 7% for NFLP_CD was low, much lower than the floor value of 38 um to 45 um for NFL thickness. These results indicate that NFLP_CD was a good basis for predicting and simulating visual fields, and that our simulation approach is workable.

An important metric for the performance of a simulation is the level of agreement with the actual quantity. We found that the agreement between NFLP_MD and VF_MD were good in the early and moderate PG stages. However, NFLP_MD tended to underestimate VF damage in the advanced PG stage. One reason for this discrepancy is the −23 dB limit we placed on the minimum value of sector NFLP_simVF to avoid extremely negative dB values that could be obtained when NFLP_CD is near the floor. This is 10 dB higher on the lower limit for actual VF total deviation of −33 dB on the Humphrey Field Analyzer. This limit was unavoidable—without it, the reproducibility of the simulated VF would be very poor in severe glaucoma eyes. Near the end stage of glaucoma damage, any small error in the NFLP_CD measurement or deviation in the simulation model (e.g., reference and floor fraction values) becomes magnified in the dB conversion calculation. Thus, the use of the NFLP-based VF simulation in disease staging needs to be done with caution—eyes suspected of having severe glaucoma need an actual VF for accurate staging.

In terms of the location of glaucoma damage, the agreement between the simulated and actual VF sector maps were good; as shown in the analysis of worst sector identification and the patterns of loss in the various stages of glaucoma severity. Locating VF loss is clinically important because damage in the paracentral sectors (1 & 2) are much more important to patient function than damage in the peripheral sectors (5, 6, 7, 8).

Looking at the structural aspect, we found that NFLP_MD had a better diagnostic accuracy than NFL thickness in detecting glaucoma. One possible reason is that OCTA might be detecting reduced perfusion associated with lower metabolism in dysfunctional retinal ganglion cells before they undergo apoptosis and cause structural thinning. Previous studies also indicated that OCTA may be able to detect glaucoma at an earlier stage. Akii et al. showed the disc and peripapillary retinal vessel density had a better diagnostic accuracy (AROC=0.956) than NFL thickness (AROC 0.772) in differentiating between PPG and normal groups. See Akil H, Huang A S, Francis B A, Sadda S R, Chopra V. Retinal vessel density from optical coherence tomography angiography to differentiate early glaucoma, pre-perimetric glaucoma and normal eyes. PLoS One 2017; 12:e0170476. Yarmohammadi et al found disc and peripapillary retinal vessel density had a better AROC (0.84) than NFL thickness (0.77) in differentiating fellow eyes of unilateral glaucoma from normal eyes. See Yarmohammadi A, Zangwill L M, Manalastas P I C, et al. Peripapillary and Macular Vessel Density in Patients with Primary Open-Angle Glaucoma and Unilateral Visual Field Loss. Ophthalmology 2018; 125:578-587.

We were surprised to further find that NFLP_MD had higher diagnostic sensitivity than NFLP_CD. Although the difference was not statistically significant, it was impressive that NFLP_MD had almost perfect diagnostic sensitivity. One possible explanation is that averaging the sector NFLP_CD values on a dB scale accentuates focal defect. Averaged on a linear scale, an isolated 90% loss in 1 out of 8 sectors (ignoring weighting) would average to −0.52 dB loss, versus on a dB scale, where the focal −10 dB loss (equal to 90% loss) in 1 out 8 sectors would average a −1.25 dB loss. Furthermore, weighting by VF area emphasizes the inferior and superior arcuate areas most often affected by early glaucoma. These possible advantages of NFLP_MD in early glaucoma detection deserve further study with a larger sample of very early glaucoma (PPG) participants.

The primary motivation of this simulation project was to improve the monitoring of glaucoma disease progression. The results here show that the simulated VF has the potential for achieving that goal. There was a high correlation between NFLP_MD and VF_MD and the correlation appeared to exist through all stages of glaucoma severity. The reproducibility of NFLP_MD was better than VF_MD, indicating a potential for earlier detection of statistically significant progression trends. What has been achieved here represents a first step—method development and preliminary validation. A large longitudinal study will be needed to determine if the simulated VF could identify patients with rapid glaucoma progression earlier than actual VF, and whether the rate of progression measured by the simulated VF agree well with actual VF.

In conclusion, we have developed a method to simulate VF based on OCTA NFLP measurements. The simulated VF correlated well with actual VF and is more reproducible than actual VF, thus holding promise for improving the monitoring of glaucoma progression. The VF simulation may also be useful in diagnosing or detecting early glaucoma, and in assessing the location and severity of glaucoma damage in patients who cannot be reliably tested with traditional perimetry methods.

Example OCT and/or OCTA Image Processing System

Figure 16:
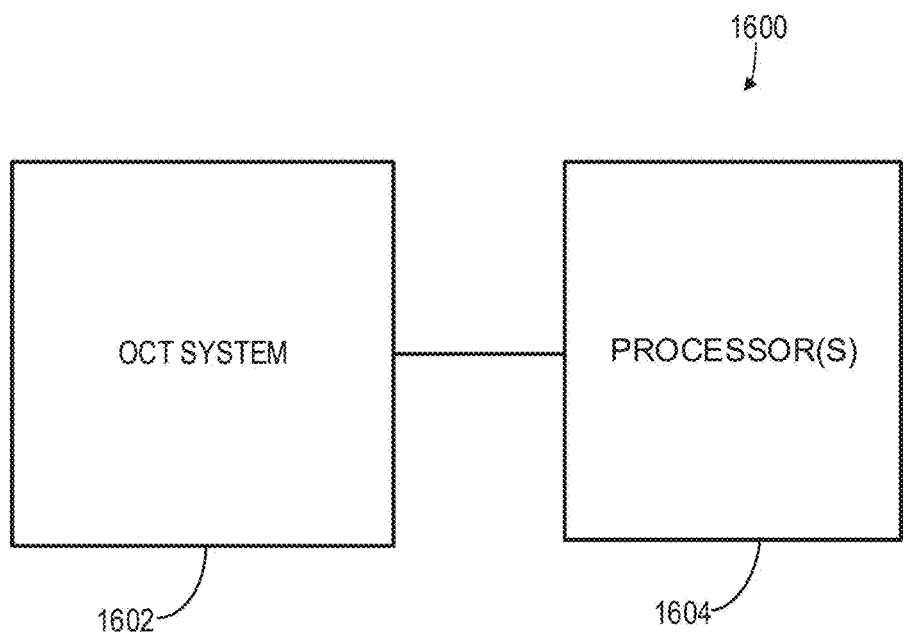
FIG. 16 schematically shows an example system for visual field simulation using OCT and/or OCTA, in accordance with various embodiments.

FIG. 16 schematically shows an example system 1600 for OCT image processing in accordance with various embodiments. System 1600 comprises an OCT system 1602 configured to acquire an OCT image comprising OCT interferograms and one or more processors or computing systems 1604 that are configured to implement the various processing routines described herein. OCT system 1600 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods and processes for HDR-OCTA described above, can be implemented as a computer application, computer service, computer API, computer library, and/or other computer program product.

Figure 17:
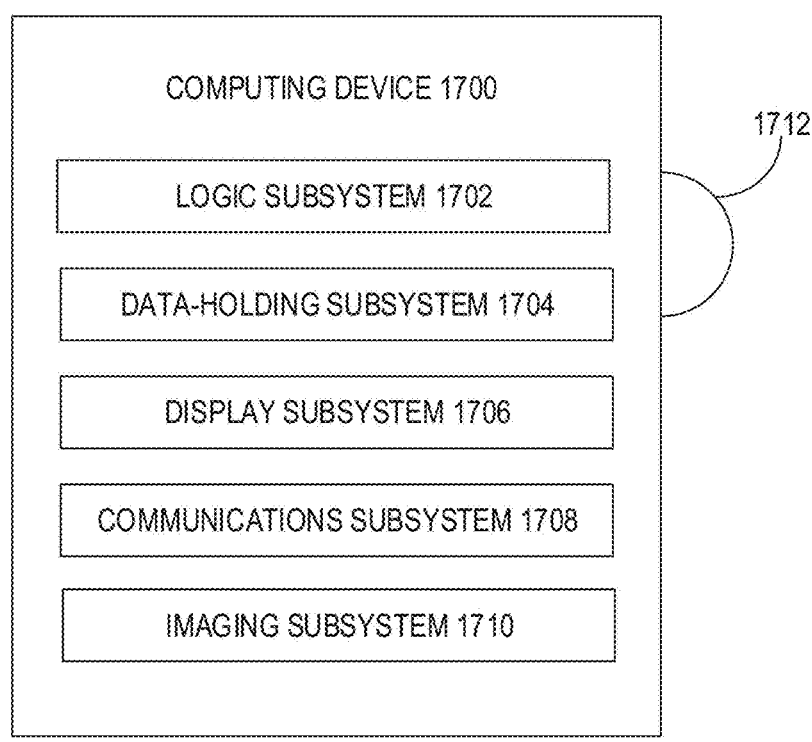
FIG. 17 schematically shows an example of a computing system in accordance with the disclosure.

FIG. 17 schematically shows a non-limiting computing device 1700 that can perform one or more of the above described methods and processes. For example, computing device 1700 can represent a processor included in system 1600 described above, and can be operatively coupled to, in communication with, or included in an OCT system or OCT image acquisition apparatus. Computing device 1700 is shown in simplified form. It is to be understood that virtually any computer architecture can be used without departing from the scope of this disclosure. In different embodiments, computing device 1700 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1700 includes a logic subsystem 1702 and a data-holding subsystem 1704. Computing device 1700 can optionally include a display subsystem 1706, a communication subsystem 1708, an imaging subsystem 1710, and/or other components not shown in FIG. 17. Computing device 1700 can also optionally include user input devices such as manually actuated buttons, switches, keyboards, mice, game controllers, cameras, microphones, and/or touch screens, for example.

Logic subsystem 1702 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1704 can include one or more physical, non-transitory, devices configured to hold data and/or instructions executable by the logic subsystem to implement the herein described methods and processes. When such methods and processes are implemented, the state of data-holding subsystem 1704 can be transformed (e.g., to hold different data).

Data-holding subsystem 1704 can include removable media and/or built-in devices. Data-holding subsystem 1704 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1704 can include devices with one or more of the following characteristics: volatile, nonvolatile, dynamic, static, read/write, read-only, random access, sequential access, location addressable, file addressable, and content addressable. In some embodiments, logic subsystem 1702 and data-holding subsystem 1704 can be integrated into one or more common devices, such as an application specific integrated circuit or a system on a chip.

FIG. 17 also shows an aspect of the data-holding subsystem in the form of removable computer-readable storage media 1712, which can be used to store and/or transfer data and/or instructions executable to implement the herein described methods and processes. Removable computer-readable storage media 1712 can take the form of CDs, DVDs, HD-DVDs, Blu-Ray Discs, EEPROMs, flash memory cards, USB storage devices, and/or floppy disks, among others.

When included, display subsystem 1706 can be used to present a visual representation of data held by data-holding subsystem 1704. As the herein described methods and processes change the data held by the data-holding subsystem, and thus transform the state of the data-holding subsystem, the state of display subsystem 1706 can likewise be transformed to visually represent changes in the underlying data. Display subsystem 1706 can include one or more display devices utilizing virtually any type of technology. Such display devices can be combined with logic subsystem 1702 and/or data-holding subsystem 1704 in a shared enclosure, or such display devices can be peripheral display devices.

When included, communication subsystem 1708 can be configured to communicatively couple computing device 1700 with one or more other computing devices. Communication subsystem 1708 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1700 to send and/or receive messages to and/or from other devices via a network such as the Internet.

When included, imaging subsystem 1710 can be used acquire and/or process any suitable image data from various sensors or imaging devices in communication with computing device 1700. For example, imaging subsystem 1710 can be configured to acquire OCT image data, e.g., interferograms, as part of an OCT system, e.g., OCT system 1602 described above. Imaging subsystem 1710 can be combined with logic subsystem 1702 and/or data-holding subsystem 1704 in a shared enclosure, or such imaging subsystems can comprise periphery imaging devices. Data received from the imaging subsystem can be held by data-holding subsystem 1704 and/or removable computer-readable storage media 1712, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computer-implemented method comprising:
   receiving an image dataset that corresponds to an optical coherence tomography (OCT) scan or an OCT angiography (OCTA) scan of an eye;
   generating a map for a parameter based on the image dataset;
   dividing the map into multiple sector maps that correspond to predefined visual field sectors;
   determining respective average values of the parameter within each of the individual sector maps;
   applying a logarithmic decibel transformation to the average values, thereby generating respective simVF sector values;
   determining a weighted logarithmic average from the respective simVF sector values; and applying a linear or nonlinear transformation to the weighted logarithmic average, thereby generating a simVF mean deviation (MD) value in dB scale.

2. The method of claim 1, wherein, to determine the weighted logarithmic average, values of the respective simVR sector maps are weighted by weights which correspond to a visual field area.

3. The method of claim 1, wherein, to determine the weighted logarithmic average, values of the respective simVR sector maps are weighted according to an area in the cerebral visual cortex.

4. The method of claim 1, wherein the image dataset corresponds to the OCT scan and the map for the parameter includes a structural thickness map.

5. The method of claim 4, wherein the structural thickness map includes a peripapillary nerve fiber layer (NFL) thickness map, a circumpapillary NFL thickness map, or a macular ganglion cell complex (GCC) thickness map, or a combination thereof.

6. The method of claim 5, wherein the OCT scan is of an optic nerve head and surrounding retina of the eye.

7. The method of claim 6, further comprising extracting a thickness profile from the structural thickness map at a distance or range of distances from a center of the optic nerve head, wherein the average value corresponds to an average thickness value for a portion of the thickness profile that is within each sector map.

8. The method of claim 4, further comprising applying an offset to the average values prior to applying the logarithmic decibel transformation.

9. The method of claim 1, wherein the applying the linear or nonlinear transformation to the weighted logarithmic average includes applying a regression formula derived from population data.

10. The method of claim 1, wherein the image dataset corresponds to the OCTA scan and the map for the parameter includes an OCTA perfusion map.

11. The method of claim 10, wherein generating the OCTA perfusion map includes:
segmenting a retinal layer within the image dataset;
generating an en face angiogram from the segmented retinal layer; and
generating the OCTA perfusion map from the en face angiogram.

12. The method of claim 10, wherein the OCTA perfusion map includes a retinal nerve fiber layer plexus (NFLP) capillary density map or a macular superficial vascular complex (SVC) vessel density (VD) map.

13. A computer-implemented method comprising:
receiving an OCTA image dataset for an optic nerve head (ONH) and surrounding peripapillary retina;
generating an OCTA perfusion map from the OCTA image dataset;
dividing the OCTA perfusion map into a plurality of sectors that correspond to predefined visual field (VF) sectors;
calculating average perfusion values for respective individual sectors of the plurality of sectors;
offsetting the average perfusion values in the individual sectors to account for floor value effects;
transforming the offsetted average perfusion values to a logarithmic decibel (dB) scale, thereby generating a set of perfusion-simulated VF values;
converting the set of perfusion-simulated VF values to simulated sector visual field deviation values based on population data;
calculating a weighted logarithmic average of the simulated sector visual field deviation values; and
converting the weighted logarithmic average of the simulated sector visual field deviation values to a VF mean deviation (MD) value based on the population data.

14. The method of claim 13, wherein the dividing includes segmenting the retinal nerve fiber layer plexus (NFLP) or the macular superficial vascular complex (SVC).

15. The method of claim 13, wherein the OCTA perfusion map includes a NFLP capillary density map or a macular superficial vascular complex (SVC) vessel density (VD) map.

16. The method of claim 13, wherein weights of the individual sectors for the weighted logarithmic average are proportional to a number of VF test points in the corresponding VF sector.

17. The method of claim 13, wherein generating the OCTA perfusion map includes:
segmenting a retinal layer within the image dataset;
generating an en face angiogram from the segmented retinal layer; and
generating the OCTA perfusion map based on the en face angiogram.

18. A system comprising:
an optical coherence tomography (OCT) system to acquire an image dataset for an eye, wherein the image dataset is an OCT dataset or an OCTA dataset;
a logic subsystem; and
a data holding subsystem comprising machine-readable instructions stored thereon that are executable by the logic subsystem to:
generate a map for a parameter based on the image dataset;
divide the map into multiple sector maps that correspond to predefined visual field sectors;
determine respective average values of the parameter within the individual sector maps;
apply a logarithmic decibel transformation to the average values to generate respective simVF sector values;
determine a weighted logarithmic average from the respective simVF sector values; and
apply a linear or nonlinear transformation to the weighted logarithmic average to generate a simVF mean deviation (MD) value in dB scale.

19. The system of claim 18, wherein, to determine the weighted logarithmic average, values of the respective simVR sector maps are weighted by weights which correspond to a visual field area.

20. The system of claim 18, wherein, to determine the weighted logarithmic average, values of the respective simVR sector maps are weighted according to an area in the cerebral visual cortex.

21. The system of claim 18, wherein the image dataset is the OCT dataset and the map for the parameter includes a structural thickness map.

22. The system of claim 21, wherein the structural thickness map includes a peripapillary nerve fiber layer (NFL) thickness map, a circumpapillary NFL thickness map, or a macular ganglion cell complex (GCC) thickness map, or a combination thereof.

23. The system of claim 22, wherein the logic subsystem is further to extract a thickness profile from the structural thickness map at a distance or range of distances from a center of an optic nerve head of the eye, wherein the average value corresponds to an average thickness value for a portion of the thickness profile that is within each sector map.

24. The system of claim 21, wherein the machine-readable instructions are further executable by the logic subsystem to apply an offset to the average values prior to applying the logarithmic decibel transformation.

25. The system of claim 18, wherein the linear or non-linear transformation applied to the weighted logarithmic average includes a regression formula derived from population data.

26. The system of claim 18, wherein the image dataset is the OCTA dataset and the map for the parameter includes an OCTA perfusion map.

27. The system of claim 26, wherein, to generate the OCTA perfusion map, the logic subsystem is to:
   segment a retinal layer within the image dataset;
   generate an en face angiogram from the segmented retinal layer; and
   generate the OCTA perfusion map from the en face angiogram.

28. The system of claim 26, wherein the OCTA perfusion map includes a retinal nerve fiber layer plexus (NFLP) capillary density map or a macular superficial vascular complex (SVC) vessel density (VD) map.

* * * * *